United States Patent
Caran et al.

(10) Patent No.: US 10,905,118 B2
(45) Date of Patent: Feb. 2, 2021

(54) TRISCATIONIC AMPHIPHILE COMPOUNDS, COMPOSITIONS, AND METHODS FOR MAKING SAME

(71) Applicant: James Madison Innovations, Inc., Harrisonburg, VA (US)

(72) Inventors: Kevin L. Caran, Staunton, VA (US); Kyle Seifert, Harrisonburg, VA (US)

(73) Assignee: JAMES MADISON INNOVATIONS, INC., Harrisonburg, VA (US)

( * ) Notice: Subject to any disclaimer, the term of this patent is extended or adjusted under 35 U.S.C. 154(b) by 0 days.

(21) Appl. No.: 14/922,126

(22) Filed: Oct. 24, 2015

(65) Prior Publication Data

US 2017/0135342 A1 May 18, 2017

Related U.S. Application Data

(60) Provisional application No. 62/068,575, filed on Oct. 24, 2014.

(51) Int. Cl.

| | | |
|---|---|---|
| *A01N 33/12* | (2006.01) | |
| *C09D 5/14* | (2006.01) | |
| *A61K 31/4425* | (2006.01) | |
| *A01N 43/40* | (2006.01) | |
| *A61K 31/14* | (2006.01) | |

(52) U.S. Cl.
CPC ............ *A01N 33/12* (2013.01); *A01N 43/40* (2013.01); *A61K 31/14* (2013.01); *A61K 31/4425* (2013.01); *C09D 5/14* (2013.01)

(58) Field of Classification Search
CPC .................................................... A01N 33/12
See application file for complete search history.

(56) References Cited

FOREIGN PATENT DOCUMENTS

WO    WO-2012054695 A1 * 4/2012 ........... C07C 217/58

OTHER PUBLICATIONS

"Periodic Table: Halogens." © 2012. Available from: < http://www.chemicalelements.com/groups/halogens.html >.*
Marafino, J., et al. "Colloidal and antibacterial properties of novel triple-headed, double-tailed amphiphiles: Exploring structure-activity relationships and synergistic mixtures." Available online to the public: Apr. 16, 2015. Bioorganic & Medicinal Chemistry. vol. 23, pp. 3566-35 (Year: 2015).*
Heerschap, S., et al. "Foams stabilized by tricationic amphiphilic surfactants." Available to public online: Sep. 26, 2015. Accessed Aug. 14, 2018. Cooloids and Surfaces A: Physicochem. Eng. Aspects. vol. 487, pp. 190-197. (Year: 2015).*
Lohr, H-G, et al. "Three-Dimensional Linkage by Electron Donor-Acceptor Interactions: Complexes of Organic Ammonium Halides with Triiodomethane." J. Org. Chem. (1984), vol. 49, pp. 1621-1627. (Year: 1984).*

* cited by examiner

*Primary Examiner* — John S Kenyon
(74) *Attorney, Agent, or Firm* — Leveque Intellectual Property Law, P.C.

(57) ABSTRACT

The inventive subject matter relates to compounds of Formula I and Formula II, compositions thereof, and processes for making such compounds as presently claimed and further described herein. The inventive compounds and compositions have antimicrobial properties and are useful as environmental disinfectants, topical cleansers such as topical personal care compositions, sanitizers, preservatives, in water treatment, as permanent or erodible coatings for medical devices and appliances, and in therapeutics.

12 Claims, 9 Drawing Sheets

S1, R=C₈H₁₇ (M-1,1,8)
S2, R=C₁₀H₂₁ (M-1,1,10)
S3, R=C₁₂H₂₅ (M-1,1,12)
S4, R=C₁₄H₂₉ (M-1,1,14)
S5, R=C₁₆H₃₃ (M-1,1,16)
S6, R=C₁₈H₃₇ (M-1,1,18)
S7, R=C₂₀H₄₁ (M-1,1,20)
S8, R=C₂₂H₄₅ (M-1,1,22)

TRISCATIONIC AMPHIPHILE COMPOUNDS, COMPOSITIONS, AND METHODS FOR MAKING SAME

CROSS-REFERENCE TO RELATED APPLICATIONS

This application claims benefit of U.S. Provisional Patent Application No. 62/068,575, filed Oct. 24, 2015, the entire contents of which is hereby incorporated by reference herein.

STATEMENT REGARDING FEDERALLY SPONSORED RESEARCH

This work was supported in part by National Science Foundation grants NSF-REU CHE-1062629 and CHE-0754521. The United States government has rights in the inventive subject matter by virtue of this support.

BACKGROUND OF THE INVENTIVE SUBJECT MATTER

Field of Inventive Subject Matter

The inventive subject matter relates to compounds of Formula I and Formula II, compositions thereof, and processes for making such compounds as further described herein. The inventive compounds and compositions have antimicrobial properties and are useful as environmental disinfectants, topical cleansers such as topical personal care compositions, sanitizers, preservatives, in water treatment, as permanent or erodible coatings for medical devices and appliances, and in therapeutics.

BACKGROUND

Over the last few decades, the overuse of antibiotics has decreased their effectiveness, contributing to bacterial acquired resistance. In addition, the production of novel antimicrobials continues to decrease due to low financial return. This decline in the development of novel antimicrobials, combined with the misusage and over prescription of antibiotics, has contributed to the increasing prevalence of antimicrobial-resistant infections (ARIs), especially in the hospital setting. ARIs have contributed to more than 25,000 deaths in member states of the European Union, Iceland, and Norway and 23,000 deaths in the United States. Hospitals and nursing homes are particularly prone to harboring antimicrobial-resistant organisms due to the frequent use of antimicrobial agents and influx of infected patients.

Limiting the transmission of bacteria between individuals and contaminated equipment is critical to reducing or preventing hospital-acquired infections and reducing mortality rates for patients and those that come into contact with them. Further, the development of biofilm contaminations on hospital surfaces such as urinary catheters, central venous catheters, and dental syringes is also a growing concern.

The development of effective novel disinfectants is highly desirable and is expected to reduce the transmission of pathogens and decrease the risk of infection by antibiotic resistant organisms.

The antimicrobial activity of cationic amphiphiles—compounds with hydrophobic and positively charged hydrophilic regions—was first reported in 1935. Amphiphiles continue to be utilized as antimicrobial agents in detergents, disinfectants, cosmetics, and other common household products. A large variety of novel amphiphiles has been synthesized in an effort to increase effectiveness and specificity.

SUMMARY OF THE INVENTIVE SUBJECT MATTER

Log of critical aggregation concentration and heat of aggregation for tested compounds were both inversely proportional to the length of the linear hydrocarbon chains. Antibacterial activity increased with tail length until an optimal tail length of 12 carbons per chain, above which, activity decreased. The derivatives with two 12 carbon chains had the best antibacterial activity, killing all tested strains at concentrations of 1-2 µM for Gram-positive and 4-16 µM for Gram-negative bacteria. The identity of the third head group, between trimethylammonium or pyridinium, had minimal effect on colloidal and antibacterial activity. The antibacterial activity of several binary combinations of amphiphiles from this study was higher than activity of individual amphiphiles, indicating that these combinations are synergistic. These amphiphiles are novel antibacterial agents that can be used in a variety of applications.

Thus, the presently claimed inventive subject matter relates to compounds of Formula I and Formula II, compositions thereof, and processes for making such compounds as further described herein. The inventive compounds and compositions have antimicrobial properties and are useful as environmental disinfectants, topical cleansers, sanitizers, preservatives, in water treatment, as permanent or erodible coatings for medical devices and appliances, and in therapeutics.

FORMULA I

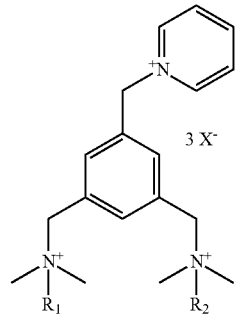

or a biologically acceptable salt, ester, or solvate thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CO_2^{(-)}$, other alkyl carboxylates, polyanions, and combinations thereof;

m equals 1 to about 22; and
n equals 1 to about 22.

FORMULA II

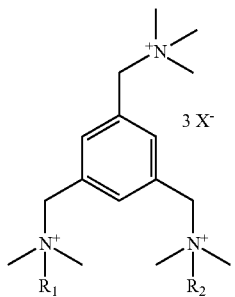

or a biologically acceptable salt, ester, or solvate thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;

m equals 1 to about 22; and n equals 1 to about 22.

DETAILED DESCRIPTION OF EMBODIMENTS

Definitions

Figure 1:
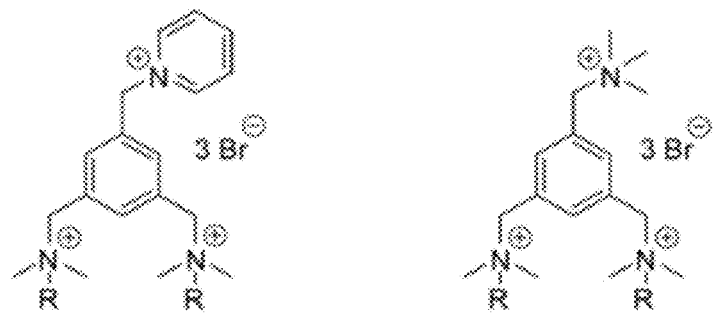
FIG. 1 is a drawing which depicts exemplary basic structures of the inventive triple-headed, double-tailed amphiphile compounds.

The terms "biologically acceptable salt, ester, or solvate" and "pharmaceutically acceptable salt, ester, or solvate" refer to a salt, ester, or solvate of a subject compound which possesses the desired biological or pharmacological activity and which is neither biologically nor otherwise undesirable. In general, a salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, basic nitrogen-containing groups that are not already quaternized can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

Regarding the formation of an ester, salt, solvate of the compounds of Formulas I and II, it will be readily understood by one of skill in the art that in some cases, these compounds cannot be so modified directly. For example and without limitation, there are presently no groups, such as an alcohol or a carboxylic acid, that could be esterified. One of skill in the art will also recognize that an ester, salt, solvate of such compounds could be made in a single-step or a multi-step process, and such insubstantial changes to Formulas I and II, which are routinely made to modify biological or pharmacological properties, are considered to be within the scope of the inventive subject matter.

It is to be understood that, in its most common form, a "reactant compound" or "intermediate" within the scope of the inventive subject matter may or may not have the reactive moiety(ies) necessary to produce a compound of the inventive subject matter. It is intended that such compound(s) may be derivatized to add one or more reactive moiety(ies) by means known to one of ordinary skill in the art. By way of example and not limitation, appropriate derivatives may be produced by hydration, halogenation, carboxylation, amination, nitration, and sulfonation.

The term "reaction product" refers to that part of a reactant compound remaining after the chemical reaction producing a covalently-linked compound of the inventive subject matter, either an intermediate or a final compound. Such chemical reactions include substitution, elimination, addition, oxidation, and reduction reactions, and involve reactive moieties such as multiple bonds; oxygen and hydroxyl; nitrogen, nitro, amide, and amine; sulfur, sulfhydryl, and sulpho; and other common groups known to one of ordinary skill in the art.

Subject Matter

The inventive subject matter relates to novel triscationic amphiphile compounds and compositions of Formula I and Formula II, as well as processes for making compounds within each genus Formula. Also within the scope of the inventive subject matter are methods of inhibiting bacterial growth comprising contacting a bacteria with any of the inventive compounds described herein.

Amphiphile structure, including size and relative number of hydrophobic tails and hydrophilic head groups, governs colloidal characteristics including the critical aggregation concentration (CAC) and thermodynamic properties. At concentrations below the CAC, amphiphiles tend to align at the air-water interface in equilibrium with dissolved monomers in solution. At concentrations above the CAC, amphiphiles form aggregates in which hydrocarbon tails interact with each other, releasing water that was formerly associated with the tails, resulting in a second equilibrium between monomers and aggregates in solution. An increase in entropy typically associated with aggregate formation is generally attributed in large part to the release of water molecules surrounding hydrophobic units to the bulk water that accompanies this process. Increasing amphiphile hydrophobicity (for example by increasing the length or number of tails) decreases water solubility, thus decreasing CAC. In contrast, additional head groups can increase amphiphile solubility, typically resulting in a higher CAC.

Applicants have determined that amphiphile structure also affects antimicrobial activity and effectiveness. There is often a direct relationship between amphiphile tail length and the minimum inhibitory concentration (MIC), the lowest concentration at which an antimicrobial is able to inhibit bacterial growth. Typically, as tail length increases the MIC decreases until an optimal tail length is reached, while antibacterial activity then begins to decrease for amphiphiles with tail lengths exceeding the optimal length.

The number, type and variations in spacing between head group(s) also affects antibacterial activity. However, Applicants have determined that the relationship between head group structure and function is not as straightforward. Increasing the number of head groups can increase or decrease the MIC depending on the structure of the head group and counterion. Different amphiphile core structures and variations in spacing between head groups can also impact the MIC. When comparing spacing between head groups, amphiphiles with a 5-carbon spacer between two cationic head groups were found to be the most biologically active.

Applicants have also determined that some mixtures of two or more amphiphiles exhibit synergy—the inhibition of bacteria at lower concentrations than when each amphiphile is used separately. By decreasing the required concentration of compounds, combination therapy reduces the potential for, or degree of, adverse side effects and increases the effectiveness of antibacterial agents. The improved efficacy of synergistic combinations has contributed to the improvement of hand disinfectants and effective treatment for patients with ARIs.

Double-tailed compounds. The inventive subject matter comprises the synthesis, as well as the colloidal, antibacterial, and synergistic characteristics, for two novel series of triple headed, double tailed amphiphiles, referred to herein as the M-P and M-I series and depicted in FIG. 1. Compounds are named as follows: M-X,n,n where M refers to the Mesitylene core, and X and n represent the attached groups: P indicates a pyridinium; a number indicates the number of carbon atoms in the alkyl group of a dimethylalkylammonium, e.g., 1=trimethylammonium; 8 octyldimethylammonium.

Exemplary amphiphiles in this group consist of three cationic head groups connected to a mesitylene core. Two of the head groups are trimethylammoniums that further connect to hydrocarbon tails varying in length from 1 to 22 carbons, preferably from 8 to 16 carbons. Although both series of amphiphiles are similar in structure to conventional Gemini amphiphiles, they are novel due to a pyridinium head group for the M-P series and a trimethylammonium head group for the M-1 series.

Figure 2:
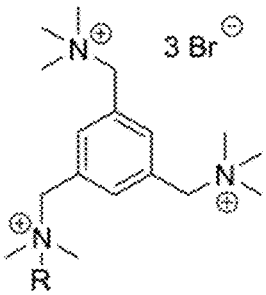
FIG. 2 is a drawing which depicts exemplary basic structures of exemplary triple-headed, single-tailed amphiphile compounds.

Single-tailed compounds. The inventive subject matter further comprises the synthesis, as well as the colloidal, antibacterial, and synergistic characteristics, for a novel series of triple headed, single tailed amphiphiles, referred to herein as the M-1,1,n series and depicted in FIG. 2. Compounds are named as follows: M-1,1,n where M refers to the Mesitylene core, and a number (n or 1) indicates the number of carbon atoms in the alkyl group of a benzylic dimethyl-alkyl ammonium (e.g., 1=trimethylammonium; 8=octyldimethylammonium). Exemplary amphiphiles in this group consist of three cationic head groups connected to a mesitylene core. Two of the head groups are trimethylammoniums, one, and only one, of which connects to a hydrocarbon tail varying in length found from 8 to 22 carbons, preferably from 14 to 22 carbons and most preferably 18 carbons.

Figure 3:
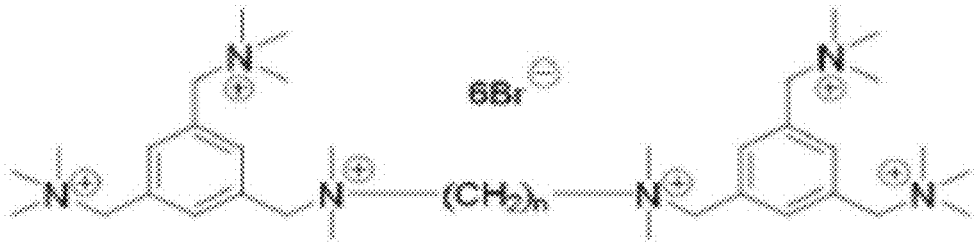
FIG. 3 is a drawing which depicts exemplary basic structures of exemplary inventive bolaamphiphile compounds.

Bolaamphiphile compounds. The inventive subject matter further comprises the synthesis, as well as the colloidal, antibacterial, and synergistic characteristics, for a novel series of compounds which are related to the compounds of Formulas I and II, in that a bolaamphiphile molecule is essentially two molecules selected from the inventive single-tailed and/or double-tailed compounds which are joined together through their respective hydrophobic tail groups. Exemplary, non-limiting bolaamphiphiles are shown in FIG. 3.

Figure 4:
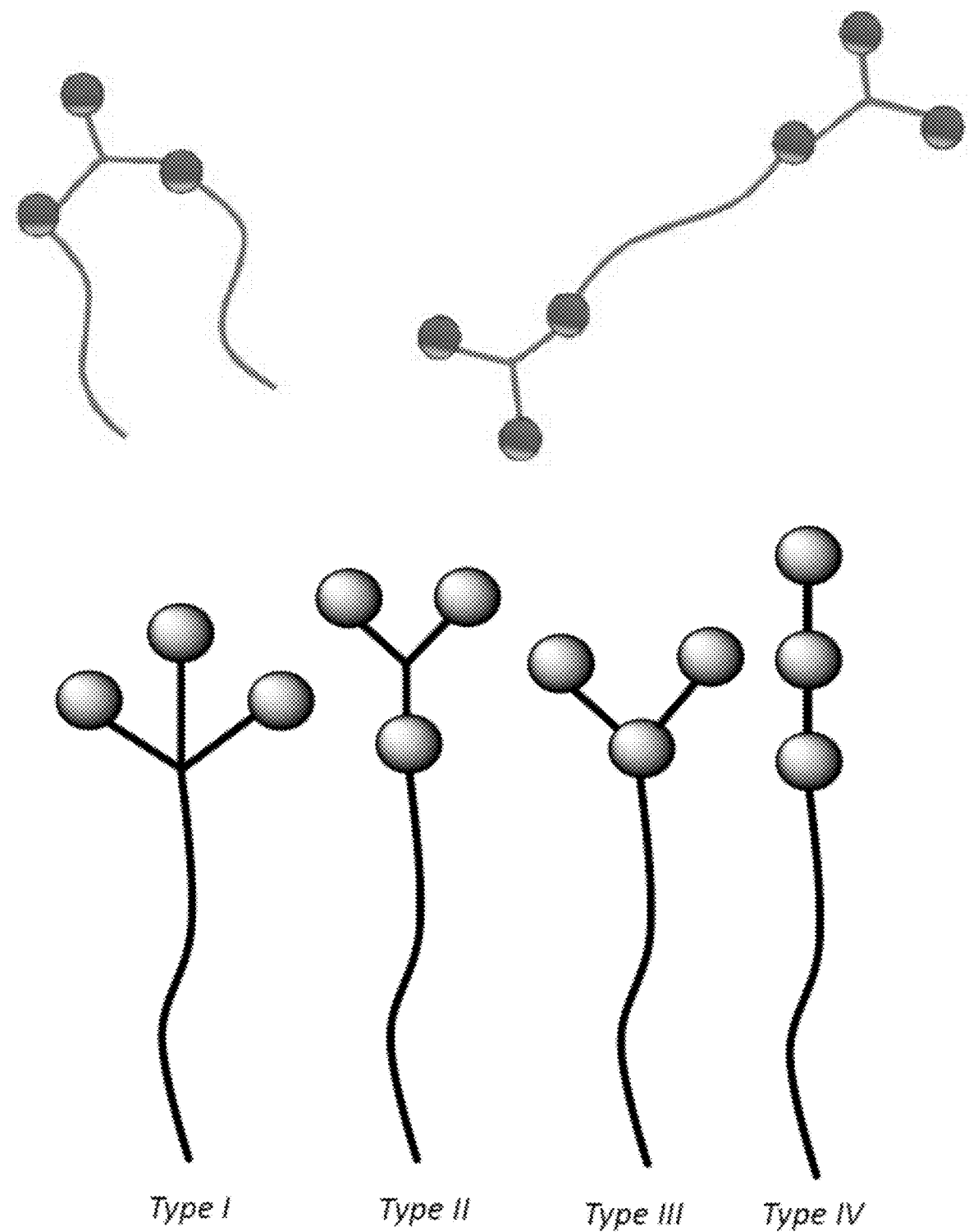
FIG. 4 is a drawing which depicts the general architectural structure for triple-headed, double-tailed amphiphiles and triple-headed bolaamphiphile compounds, as well as architectural variants for triple-headed, single-tailed amphiphiles, Types I-IV.

Shown in FIG. 4 are the three types inventive compounds. Depicted in the upper left is a double-tailed amphiphile molecule. Depicted in the upper right is a bolaamphiphile molecule. Depicted in the lower section are single-tailed amphiphile molecules in which a branched arrangement of polar headgroups (represented as circles) allows for a non-polar tail (represented as a line) to be connected to a branch point or central core (Type I) or to a headgroup (Type II). Alternatively, headgroups can be arranged in series with the tail connected to the central (Type III) or terminal (Type IV) headgroup.

Although there may be no direct relationship between an amphiphile's colloidal and antimicrobial properties, both are clearly and profoundly affected by amphiphile structure. Developing a deeper understanding of these structure-function relationships provides insight into the mechanism by which amphiphiles interact with and inhibit bacterial growth. These particular architectures are expected to be highly effective disinfectants, likely through a mechanism that disrupts the bacterial membrane. The three cationic head groups are expected to interact with the net negative bacterial membrane, allowing the intercalation of the amphiphile's hydrophobic tails. This, in essence, appears to anchor the amphiphile in the membrane, creating disruption via the rigid mesitylene core and three cationic head groups.

To address this need, Applicants have developed two novel series of double-tailed amphiphiles, which were synthesized and for which structure-activity relationships were investigated. Log (CAC) and $\Delta H_{agg}$ each decreased linearly with increasing tail length for both series. For most of the amphiphiles tested, the MIC is significantly below the CAC, indicating amphiphile aggregation is not necessary for antibacterial activity. MIC values also indicated an optimal tail length of 12 carbons for each series as compounds 3 and 8 (M-P,12,12 and M-1,12,12) have the lowest MIC against all strains tested. Further, three binary combinations of compounds 3, 4, 5, 8, 9, and 10 exhibited synergistic relationships, demonstrating greater antibacterial activity when combined. These amphiphiles will prove useful in the medical field as surface disinfectants, antiseptics, or in topical treatments for treating or preventing infection with antibiotic-resistant organisms.

Compounds

Thus, the presently claimed inventive subject matter relates to compounds of formulas I and II:

FORMULA I

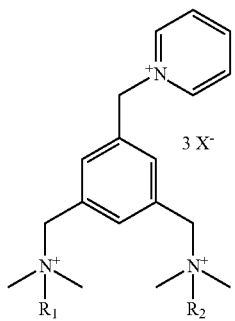

or a biologically acceptable salt, ester, or solvate thereof, wherein:
  $R_1$ is independently selected from the group consisting of straight or branched chain $C_n$ alkyl, alkenyl, or alkynyl;
  $R_2$ is independently selected from the group consisting of straight or branched chain $C_m$ alkyl, alkenyl, or alkynyl;
  X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;
  m equals 1 to about 22; and
  n equals 1 to about 22.

In a preferred embodiment, $R_1$ is independently selected from the group consisting of straight or branched chain $C_n$ alkyl; and $R_2$ is independently selected from the group consisting of straight or branched chain $C_m$ alkyl.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.

In more preferred embodiment, X is bromine.

FORMULA II

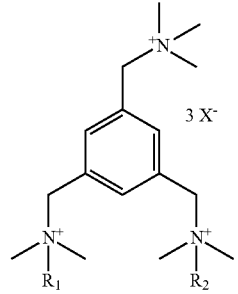

or a biologically acceptable salt, ester, or solvate thereof, wherein:
  $R_1$ is independently selected from the group consisting of straight or branched chain Ca alkyl, alkenyl, or alkynyl;
  $R_2$ is independently selected from the group consisting of straight or branched chain $C_m$ alkyl, alkenyl, or alkynyl;
  X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;
  m equals 1 to about 22; and
  n equals 1 to about 22.

In a preferred embodiment, $R_1$ is independently selected from the group consisting of straight or branched chain $C_n$ alkyl; and $R_2$ is independently selected from the group consisting of straight or branched chain $C_m$ alkyl.

More particularly, the inventive subject matter relates to a compound of Formula II, wherein m equals 2 to about 18 and n equals 2 to about 18.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.

In a more preferred embodiment, X is bromine.

The double-tailed compounds of Formulas I and II are 3+ cations, which in many situations, for example in dry form and in most solutions, are preferably balanced by any combination of anion(s) having a total charge of 3−. It is expected that the anion(s) which would be employed in many antimicrobial applications would be selected from the group consisting of carbonate, sulfate, thiosulfate, dihydrogen phosphate, fluoride, chloride, nitrate, bromide, iodide, thiocyanate, acetate, hexanoate, other alkyl carboxylates, polyanions, and combinations thereof, but the scope of the inventive subject matter is not so limited; any suitable combination of anion(s) may be used. Selection of suitable anion(s) is known to those of skill in the art.

A third class of inventive compounds, single-tailed amphiphiles, has also been developed. Such compounds are a variant of the compounds of Formulas I and II, in that a single-tailed amphiphile molecule is a compound of Formula I or Formula II, in which either (1) $R_1$ is methyl and $R_2$ is $C_{8-22}$ alkyl, preferably $C_{14-22}$ alkyl, and most preferably Cis alkyl, or (2) $R_2$ is methyl and $R_1$ is $C_{8-22}$ alkyl, preferably $C_{14-22}$ alkyl, and most preferably Cis alkyl.

A fourth class of inventive compounds, referred to by Applicants as bolaamphiphiles, has also been developed. Such compounds are related to the compounds of Formulas I and II, in that a bolaamphiphile molecule is essentially two molecules selected from the inventive single-tailed and/or double-tailed compounds joined together through their respective hydrophobic tail groups. Exemplary, non-limiting bolaamphiphiles are shown in FIG. 3. As will be readily apparent to one of skill in the art, many more compounds of the bolaamphiphile class can be made from various combinations of two single-tailed and/or double-tailed molecules joined together.

Antimicrobial Uses

As contemplated at the time of filing this application, Applicants expect that the antimicrobial properties of the inventive compounds and compositions will find a primary use as environmental disinfectants and sanitizers, addressing the needs described above for limiting the transmission of bacteria between individuals and contaminated equipment, as well as the increasing prevalence of antimicrobial-resistant infections, in critical health care settings such as hospitals and nursing homes. Thus, within the scope of the inventive subject matter are methods of inhibiting bacterial growth comprising contacting a bacteria with any of the inventive compounds or compositions described herein.

Additional uses for the inventive compounds and compositions include topical personal care compositions; as permanent or erodible coatings for medical devices and appliances; preservatives; in water treatment; and as therapeutics.

Exemplary but non-limiting topical uses may include deodorants, antiperspirants, antiperspirant/deodorants, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, and drug delivery systems for topical application of medicinal compositions that are to be applied to the skin.

Exemplary but non-limiting uses as coatings, whether permanent or erodible, for articles of manufacture such as medical devices and appliances, include coatings for medical equipment, appliances, and devices; medical supplies such as catheters, sutures and staples, syringes and needles, implants, prosthetics, drains, stents, meshes, cardiac valves, dressings, pins, clamps, clips, tubings, controlled drug delivery systems, and the like; finishing of textiles and fibers; and consumer articles such as touch screens in personal electronic devices, computers, and automatic teller machines. Such articles of manufacture may be metal, glass, plastic, and/or fibers.

Processes for Making the Inventive Double-Tailed Compounds

The inventive subject matter also relates to a compound of formula I, produced by a process comprising:
(a) reacting 1,3,5-trisbromomethylbenezene with pyridine in an acetone solvent to produce a precipitate,
(b) filtering said precipitate,
(c) washing said precipitate in acetone to isolate an intermediate of Formula III

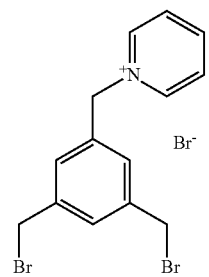

III (d) reacting said intermediate with an excess of $NMe_2$-$(CH_2)_{n-1}$—$CH_3$ in ethanol at reflux to produce the compound of Formula I, and
(e) isolating the compound of Formula I.

The inventive subject matter also relates to a compound of formula II produced by a process comprising:
(a) reacting 1,3,5-trisbromomethylbenezene with trimethylamine in an acetone/ethanol solvent to produce a precipitate, (b) heating the reaction mixture in step (a) to about 60° C. and filtering said precipitate,
(c) washing said precipitate in acetone to isolate an intermediate of Formula IV

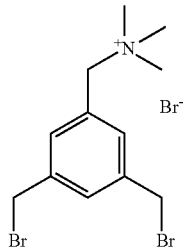

IV (d) reacting said intermediate with an excess of $NMe_2$-$(CH_2)_{n-1}$—$CH_3$ in ethanol at reflux to produce the compound of Formula II, and
(e) isolating the compound of Formula II.

Pharmaceutical Compositions

The inventive subject matter also relates to a pharmaceutical composition comprising (i) an effective amount of a compound of Formula I

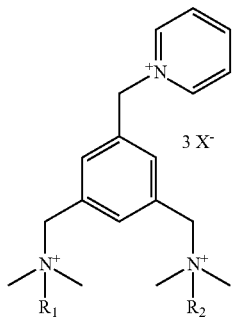

I or a pharmaceutically acceptable salt, ester, or solvate thereof, wherein:
  $R_1$ is independently selected from the group consisting of straight or branched chain $C_n$ alkyl, alkenyl, or alkynyl;
  $R_2$ is independently selected from the group consisting of straight or branched chain $C_m$ alkyl, alkenyl, or alkynyl;
  X is a counterion selected from the group consisting of $CO_3^{(2-)}$, $SO_4^{(2-)}$, $S_2O_3^{2-}$, $H_2PO_4^{(-)}$, $NO_3^{(-)}$, $F^{(-)}$, $Cl^{(-)}$, $Br^{(-)}$, N, $SCN^{(-)}$, $CH_3CO_2^{(-)}$, $CH_3CH_2CH_2CH_2CH_2CO_2^{(-)}$, other alkyl carboxylates, polyanions, and combinations thereof;
  m equals 1 to about 22;
  n equals 1 to about 22; and
(ii) a pharmaceutically acceptable carrier.

In a preferred embodiment, $R_1$ is independently selected from the group consisting of straight or branched chain $C_n$ alkyl; and $R_2$ is independently selected from the group consisting of straight or branched chain $C_m$ alkyl. More particularly, the inventive subject matter relates to a compound of Formula II, wherein m equals 2 to about 18 and n equals 2 to about 18.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.
In more preferred embodiment, X is bromine.
The inventive subject matter further relates to a pharmaceutical composition comprising (i) an effective amount of a compound of Formula II

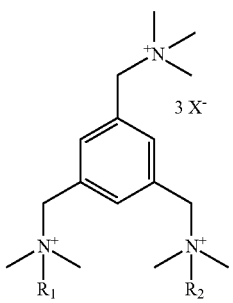

II or a pharmaceutically acceptable salt, ester, or solvate thereof, wherein:
  $R_1$ is independently selected from the group consisting of straight or branched chain $C_n$ alkyl, alkenyl, or alkynyl;
  $R_2$ is independently selected from the group consisting of straight or branched chain $C_m$ alkyl, alkenyl, or alkynyl;
  X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, N, $SCN^{(-)}$, $CH_3CO_2^{(-)}$, $CH_3CH_2CH_2CH_2CH_2CO_2^{(-)}$, other alkyl carboxylates, polyanions, and combinations thereof;
  m equals 1 to about 22;
  n equals 1 to about 22; and
(ii) a pharmaceutically acceptable carrier.

In a preferred embodiment, $R_1$ is independently selected from the group consisting of straight or branched chain $C_n$ alkyl; and $R_2$ is independently selected from the group consisting of straight or branched chain $C_m$ alkyl.

In a more preferred embodiment, $R_1$ is independently selected from the group consisting of straight chain $C_{2-18}$ alkyl; and $R_2$ is independently selected from the group consisting of straight chain $C_{2-18}$ alkyl.

In a more preferred embodiment, $R_1$ is independently selected from the group consisting of straight chain $C_{8-16}$ alkyl; and $R_2$ is independently selected from the group consisting of straight chain $C_{8-16}$ alkyl.

In a more preferred embodiment, $R_1$ is independently selected from the group consisting of straight chain $C_{10-14}$ alkyl; and $R_2$ is independently selected from the group consisting of straight chain $C_{10-14}$ alkyl.

In a more preferred embodiment, $R_1$ is $C_{12}$ alkyl; and $R_2$ is $C_{12}$ alkyl.

In another preferred embodiment, X is halogen.
In a more preferred embodiment, X is bromine.
The compounds of Formulas I and II are 3+ cations, and as discussed above are preferably balanced by any combination of anion(s) having a total charge of 3-. Anions suitable for pharmaceutical applications are known to those of skill in the art.

The novel pharmaceutical compositions of the inventive subject matter include a therapeutically effective amount of the active agent indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the inventive subject matter.

The compounds of the inventive subject matter are preferably delivered to the patient by means of a pharmaceutically acceptable carrier. Such carriers are well known in the art and generally will be in either solid or liquid form. Solid form pharmaceutical preparations which may be prepared according to the inventive subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired.

Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that compounds of the inventive subject matter will display significant adverse interactions with other synthetic or naturally occurring substances. Thus, an inventive compound or composition may be administered in combination with other antimicrobial compounds and compositions. In particular the inventive compounds and compositions may be administered or otherwise used in combination with other inventive compounds and compositions, or other antimicrobial substances. For example, an inventive compound or composition may be administered in combination with any one the large number of antibiotics known in the art.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the inventive subject matter.

Therapeutic Route(s) of Administration

Therapeutic route(s) of administration of the compounds and compositions of the inventive subject matter are well known to those skilled in the art (see, for example, "Remington's Pharmaceutical Sciences", 18th Edition, Chapter 86, pp. 1581-1592, Mack Publishing Company, 1990). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

The compounds and compositions may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in a preferred embodiment, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bio-erodible particles or beads and depot injections, are also known to those skilled in the art.

Synthesis of Inventive Compounds

The inventive compounds may be readily prepared by standard techniques of organic chemistry, utilizing the general synthetic pathways depicted below.

In the preparation of the compounds of the inventive subject matter, one skilled in the art will understand that one may need to protect or block various reactive functionalities on the starting compounds or intermediates while a desired reaction is carried out on other portions of the molecule.

17

After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the inventive subject matter.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

Two novel series of tris-cationic, tripled-headed, double-tailed amphiphiles were synthesized and the effects of tail length and head group composition on the critical aggregation concentration (CAC), thermodynamic parameters, and minimum inhibitory concentration (MIC) against six bacterial strains were investigated.

Amphiphiles tested are composed of a benzene core with three benzylic ammonium bromide groups, two of which have alkyl chains, each 8 to 16 carbons in length as tested. The third head group is a trimethylammonium or pyridinium. Synergistic antibacterial combinations of these amphiphiles were also identified.

18

EXAMPLES

The following examples are illustrative of the inventive subject matter and are not intended to be limitations thereon. Unless otherwise indicated, all percentages are based upon 100% by weight of the final composition.

Example 1

Preparation of Triscationic Double-Tailed Amphiphiles

The following example illustrates the preparation of preferred active agents provided according to the double-tailed inventive subject matter. Compound numbers corresponding to the Schemes and Tables herein are indicated in bold.

Each of the amphiphiles in this application was prepared in two steps by subsequent Menshutkin reactions, as shown in Scheme 1.

Scheme 1. Synthesis of triple-headed, double-tailed amphiphiles

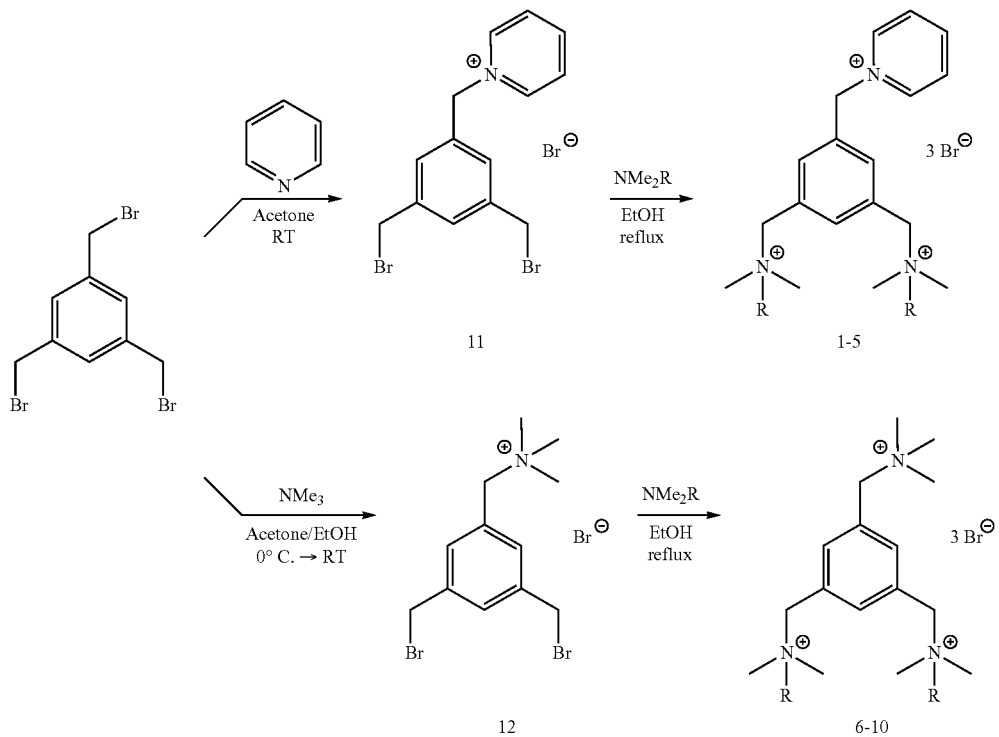

To prepare the M-P series (compounds 1-5), 1,3,5-tris-bromomethylbenezene was reacted with a slight excess of pyridine resulting in intermediate 11 (77% yield). Selective reaction at just one of the three equivalent benzylic positions was aided by the decreased solubility of the desired product, which precipitates from the reaction mixture upon formation. Filtration and washing with acetone provides compound 11 in sufficient purity for the next synthetic step. Substitution of the two remaining benzylic bromides on 11 was accomplished using excess dimethylalkylamine ($NMe_2(CH_2)_{n-1}CH_3$, where n=8, 10, 12, 14 or 16) in ethanol at reflux producing the M-P series of amphiphilic products 1-5 (63-92% yield).

To prepare the M-1 series (compounds 6-10), 1,3,5 tris-bromomethylbenezene was reacted with a slight excess of trimethylamine resulting in intermediate 12 (37% yield). This reaction produces primarily 12, along with a highly insoluble biscationic byproduct (a result of two benzylic bromides being substituted with trimethylamine), which can be effectively removed by an extraction protocol as detailed in the experimental section. Substitution of the two remaining benzylic bromides on 12 was accomplished using excess dimethylalkylamine (NMe$_2$(CH$_2$)$_{n-1}$CH$_3$, where n=8, 10, 12, 14, 16) in ethanol at reflux producing the M-1 series of amphiphilic products 6-10 (20-75% yield).

Preparation of Bolaamphiphiles

As shown in Scheme 2, reactions of dibromoalkane (C$_6$H$_{12}$Br$_2$ through C$_{12}$H$_{24}$Br$_2$) with large excess of dimethylamine, 40% aqueous, in THF gave bis(dimethylamino) alkanes alkyldimethylamine 18-21. These intermediates were then reacted with 2.5 equivalents of compound 2 (M-1,1) in ethanol at RT to give 22-25 [M-1,1]-n-[M-1,1].

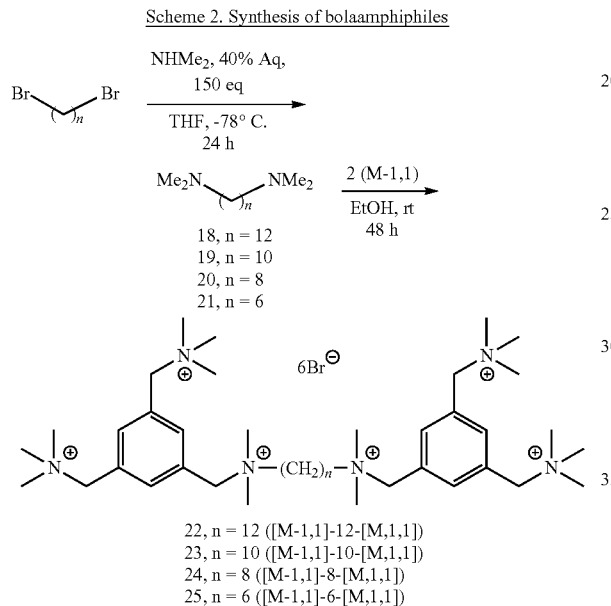

Preparation of Triscationic Single-Tailed Amphiphiles

The following example illustrates the preparation of preferred single-tailed active agents provided according to the inventive subject matter. Compound numbers corresponding to the Schemes and Tables herein are indicated in bold.

Each of the single-tailed amphiphiles in this application was prepared in two steps by subsequent Menshutkin reactions, as shown in Scheme 3.

Synthesis of Intermediate S9

1,3,5-tris(bromomethyl)benezene (1.0 g, 2.8 mmol) was dissolved in acetone at room temperature in a round bottom flask (RBF). The solution was cooled on an ice bath for 30 minutes, equipped with a stir-bar, and attached to an addition funnel. An ethanolic trimethylamine solution (1.2 mL, 5.6 mmol) was dissolved in acetone and cooled on an ice bath for 30 minutes. The trimethylamine solution was added drop-wise to the stirring solution of 1,3,5-tris(bromomethyl) benzene. The reaction was run overnight, and warmed slowly to room temperature. A white precipitate containing a mixture of 9 and a monocationic side product formed. The crude reaction mixture was vacuum filtered and resuspended in a solution of acetone and ethanol (100:3), heated to 60° C., stirred for at least 30 minutes, vacuum filtered, and dried under vacuum to produce intermediate 9 (856 mg, 64%, white solid).

Synthesis of S1-S8: General Protocol

Intermediate S9 was added to a two neck round bottom flask and dissolved in ethanol. The flask was equipped with a stir bar and a water-cooled condenser. Alkyl amine (NMe2 (CH2)n-1CH3, where n=8, 10, 12, 14, 16, 18, 20, or 22) was added slowly to the flask via syringe. The reaction was heated to 80° C. and run overnight at reflux. Volatile materials were removed under a flow of N2 (g). The resulting crude solid was suspended in acetone, vacuum filtered, and dried in under vacuum to yield the solid amphiphile product (S1-S8).

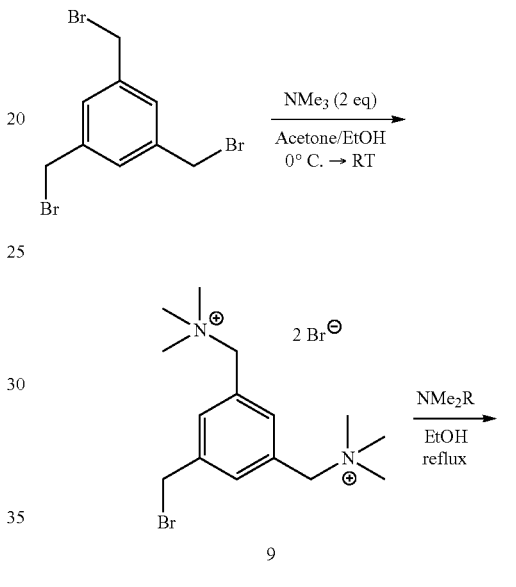

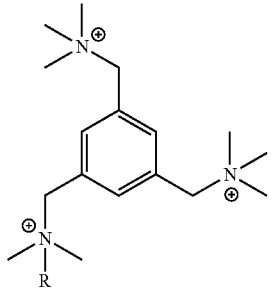

Example 2

Critical Aggregation Concentration and Heat of Aggregation Formation

Isothermal titration calorimetry (ITC) was used to determine the critical aggregation concentration (CAC) and the thermodynamic parameters at 37° C. associated with aggregate formation for each double-tailed amphiphile for the M-P and M-1 series, as shown in Table 1. Data for single-tailed amphiphiles for the M-1,1,n series, is shown in Table 2.

TABLE 1

| M-P | M-1 | Tail Length | CMC [mM] | | $\Delta H_{mic}$ (kJ/mol) | | $\Delta G_{mic}$ (kJ/mol) | | $-T\Delta S_{mic}$ (kJ/mol) | |
|---|---|---|---|---|---|---|---|---|---|---|
| | | | M-P | M-1 | M-P | M-1 | M-P | M-1 | M-P | M-1 |
| 2 | 7 | 10,10 | 14 | 12 | −11 | −15 | −21 | −22 | 10 | 6.6 |
| 3 | 8 | 12,12 | 2.4 | 2.5 | −23 | −26 | −26 | −26 | 3.1 | 0.082 |
| 4 | 9 | 14,14 | 0.56 | 0.61 | −38 | −37 | −30 | −29 | −8.7 | −8.0 |
| 5 | 10 | 16,16 | 0.18 | 0.16 | −42 | −55 | −33 | −33 | −9.2 | −22 |

TABLE 2

| Compound | Tail Length (n for M-1, 1, n) | CAC [mM] | $\Delta H_{agg}$ (kJ/mol) | $\Delta G_{agg}$ (kJ/mol) | $-T\Delta S_{agg}$ (kJ/mol) |
|---|---|---|---|---|---|
| S4 | 14 | 21 | −10 | −20 | −10 |
| S5 | 16 | 9.2 | −14 | −22 | −8.5 |
| S6 | 18 | 5.0 | −22 | −24 | −2.4 |
| S7 | 20 | 2.0 | −28 | −26 | 1.6 |
| S8 | 22 | 0.99 | −33 | −28 | 5.1 |

Figure 5:
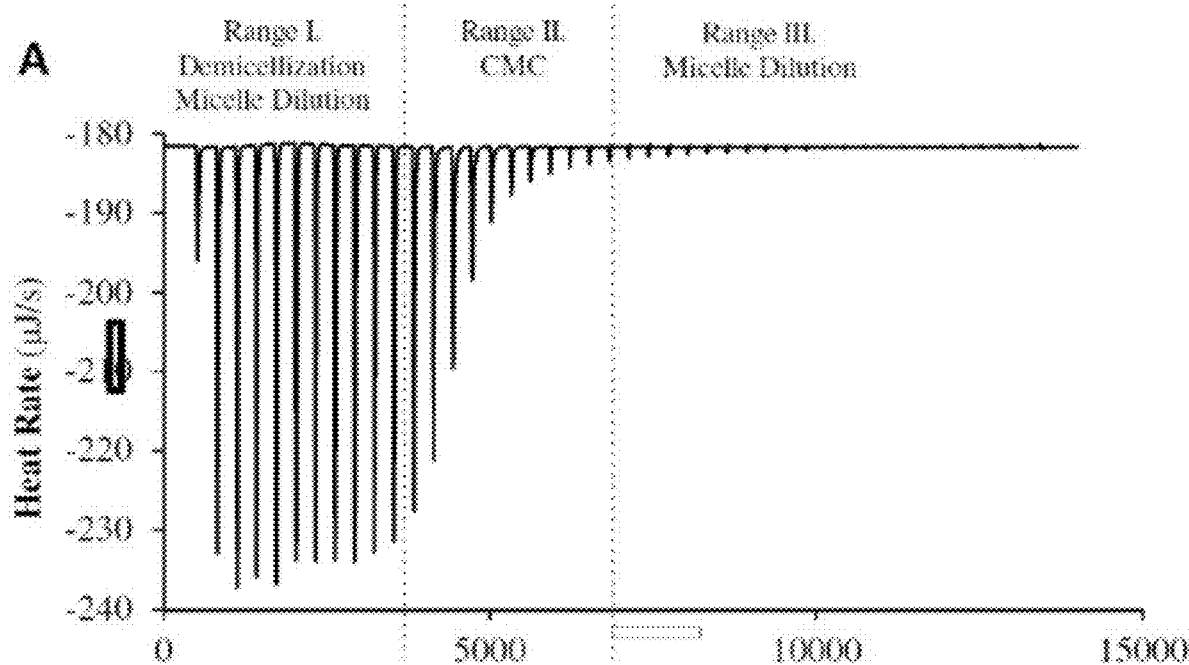
FIG. 5 is a graph which depicts the isothermal titration calorimetry heat rate for demicellization.
Figure 6:
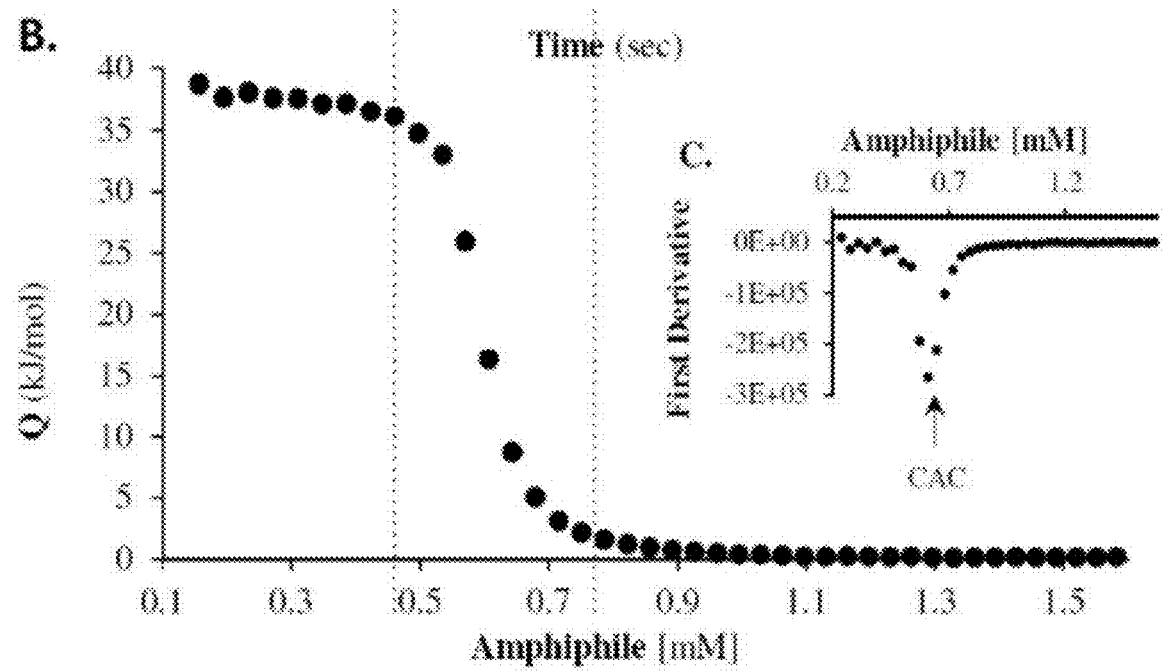
FIG. 6 is a graph which depicts integration of the isothermal titration calorimetry normalized heat per injection.

A Nano ITC was used to measure the heat change associated with the deaggregation of amphiphiles via power compensation. A concentrated aqueous solution of amphiphile (>>CAC) was titrated into a thermally controlled sample cell, initially containing pure water, in a series of discrete injections. Isothermal titration calorimetry was used to determine the critical aggregation concentration (CAC) and $\Delta H_{agg}$. Shown in FIG. 5 is the heat rate associated with each injection versus time for 9 (M-1,14,14). Shown in FIG. 6 is the integration of the heat per injection normalized by the number of moles of each injection versus the increasing concentration of amphiphile in the well. In FIG. 6, inset, CAC is determined by calculating the first derivative of the heat curve.

Typical ITC results can be divided into three ranges associated with the concentration of amphiphile in the sample cell below, at, and above the CAC, as seen for compound 9 (M-1,14,14) in FIGS. 5 and 6. During initial injections (Range I), measured heat changes are due to both the dilution of aggregates and deaggregation. This can be observed in the first 10 injections, where aggregates absorbed heat and disassociated into dissolved monomers. The heat change produced by each injection was approximately constant in this range. In Range II, injected aggregates don't fully dissociate, reducing the total absorbed heat for each subsequent injection. At concentrations well above the CAC (Range III), absorbed heat is attributed only to the dilution of aggregates and is approximately constant. The CAC was determined by the inflection point in Range II, as measured by the minimum value in the plot of CAC versus the first derivative of the heat as shown in FIG. 6, inset. Analogous results were recorded for compounds 2-5 and 7-10, the results of which are presented in Table 1. CAC and thermodynamic data were not determined for the amphiphiles with the shortest tails [1 (M-P,8,8) and 6 (M-1,8,8)] because the heat evolved during injection was above the threshold of the instrument.

Figure 7:
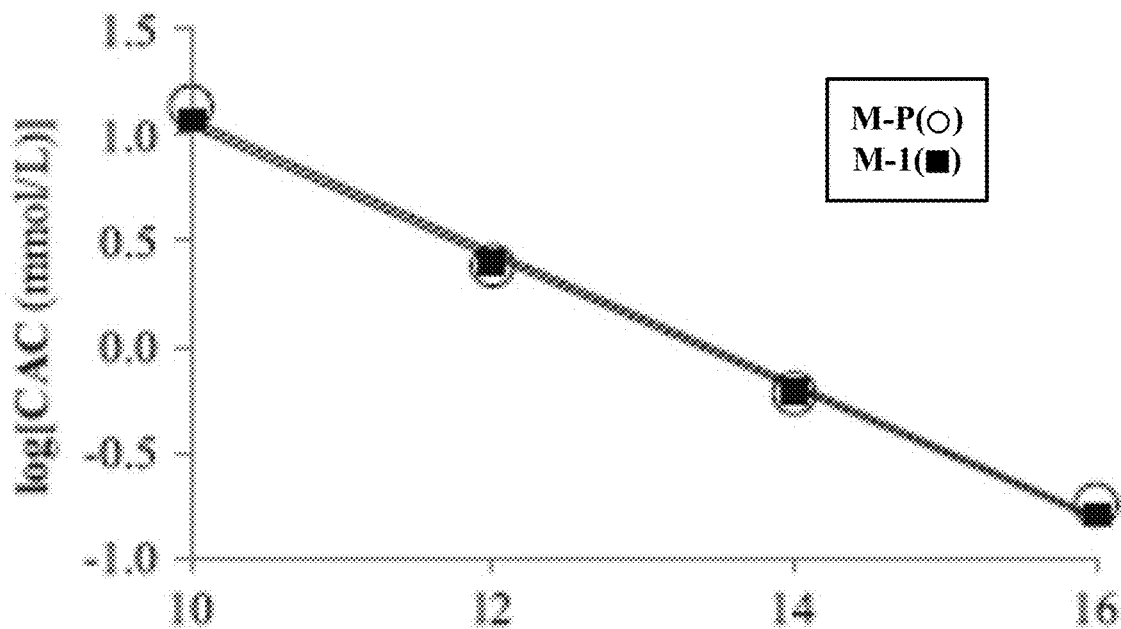
FIG. 7 is a graph which depicts a plot of log(CAC) versus tail length for tested double-tailed compounds.

As shown in Table 1, both series of compounds exhibit a decrease in CAC as tail length increases. CAC values for the M-P and M-1 series are approximately equivalent for each tail length, following a linear plot of log(CAC) versus tail length as shown in FIG. 7, according to the equation:

$$\log(CAC) = A - Bn \quad (1)$$

where A and B are constants and n is the number of carbons in each hydrocarbon tail. The dependence of CAC on tail length is the same for each series (B=0.31).

The difference between the average heat of injections in Range I, representing the total heat due to the dilution of aggregates and deaggregation, and the average heat of injections in Range III, representing the heat due solely to the dilution of aggregates, gives the heat of deaggregation, $\Delta H_{deagg}$. The $\Delta H_{deagg}$ for compound 9 (M-1,14,14) is 37 kJ/mol, corresponding to a heat of aggregate formation, $\Delta H_{agg}$, of −37 kJ/mol ($\Delta H_{agg} = -\Delta H_{deagg}$). As shown in Table 1, the negative $\Delta H_{agg}$ values indicate that aggregation is an exothermic process for all of the amphiphiles tested.

Figure 8:
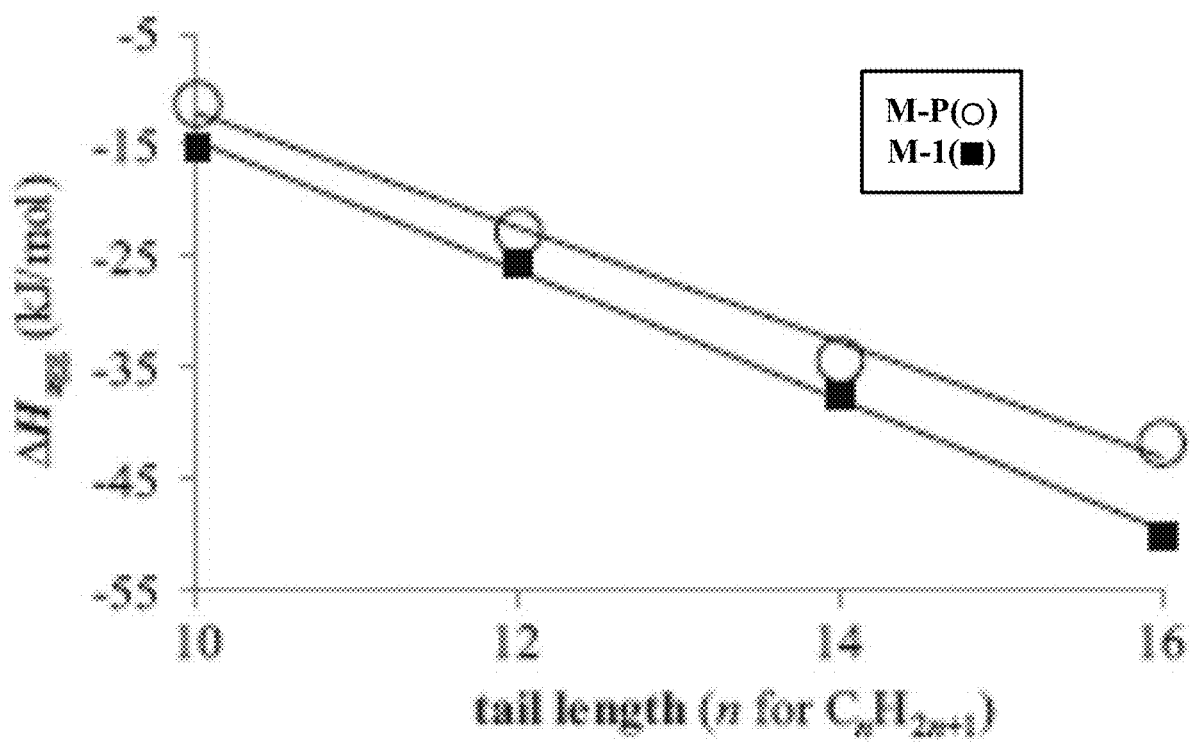
FIG. 8 is a graph which depicts a plot of $\Delta H_{agg}$ versus tail length for tested double-tailed compounds.

This is attributed to the release of heat accompanying aggregate formation from additional hydrogen bonding of water molecules joining the bulk, and from hydrocarbon tail interactions in the newly formed aggregate. Furthermore, $\Delta H_{agg}$ becomes more negative as tail length increases for both series of amphiphiles, following a linear trend shown in FIG. 8, according to the equation:

$$\Delta H_{agg} = C - Dn \quad (2)$$

where C and D are constants and n is the number of carbons in each hydrocarbon tail. The dependence of $\Delta H_{agg}$ on tail length is similar for each series (D=−5.1 for the M-P series; D=−5.8 for the M-1 series). The inverse relationship between $\Delta H_{agg}$ and amphiphile tail length is consistent with a larger amount of water released per molecule of amphiphile, as well as greater van der Waals interactions between the longer tails.

The $\Delta G_{agg}$ can be approximated for the aggregation of nonionic amphiphiles by the equation:

$$\Delta G_{agg} = RT \ln(CAC/55.5) \quad (3)$$

where the CAC represents an equilibrium between monomeric and aggregated amphiphiles. The CAC is expressed as a molar fraction: molar units divided by the molar concentration of water (55.5 mol/L). This equation changes for ionic amphiphiles due to the presence of counterions and the degree of ionization at the aggregate surface. Thus the equation is modified for an ionic amphiphile as follows:

$$\Delta G_{agg} = RT[1+(m/n)]\ln(CAC/55.5) \quad (4)$$

where m is the concentration of counterions that associate with a aggregate and n is the number of monomers that associate to form an aggregate. Since this study did not include determination of the degree of ionization or aggregate aggregation, $\Delta G_{agg}$ was approximated using equation (3), as has been done by others (see, e.g. Bhattacharya, S.; Haldar, J. Microcalorimetric and Conductivity Studies with Micelles Prepared from Multi-Headed Pyridinium Surfactants. *Langmuir.* 2005, 21, 5747-5751; Paula, S.; Süs, W.; Tuchtenhagen, J.; Blume, A. Thermodynamics of micelle formation as a function of temperature: A high sensitivity titration calorimetry study. *J. Phys. Chem.* 1995, 99, 11742-11751; and Heerklotz, H.; Seelig, J. Titration calorimetry of surfactant-membrane partitioning and membrane solubilization. *BBA-Biomembranes*. 2000, 1508, 69-85.)

Again as shown in Table 1, the $\Delta G_{agg}$ for all compounds tested is negative and becomes more negative as tail length increases. Thus the increase in chain length within a series of amphiphiles is consistent with the increased propensity to spontaneously form aggregates.

The entropy of aggregation ($\Delta S_{agg}$) is dictated by a combination of entropic factors that favor or disfavor aggregate formation and can be approximated using the Gibbs-Helmholtz equation:

$$\Delta G_{agg} = \Delta H_{agg} - T\Delta S_{agg} \quad (5)$$

The entropic contribution to $\Delta G_{agg}$, is presented as the negative of $T\Delta S_{agg}$ in Table 1. In both series, the $-T\Delta S_{agg}$ term is negative for amphiphiles with chain lengths of up to 12 carbons [2 (M-P,10,10), 3 (M-P,12,12), 7 (M-1,10,10), and 8 (M-1,12,12)]. This suggests that the entropy gained from the release of water from hydrophobic sections is greater than the decrease in entropy of amphiphiles due to the formation of aggregates. Thus the entropic factor, for amphiphiles with shorter chain lengths, contributes to the spontaneous formation (negative $\Delta G_{agg}$) of aggregates.

The $-T\Delta S_{agg}$ term is positive for double tailed amphiphiles with tail lengths exceeding 12 carbons [4 (M-P,14,14), 5 (M-P,16,16), 9 (M-1,14,14), and 10 (M-1,16,16)]. This suggests that the entropy gained from the release of water from hydrophobic units is smaller than the decrease in entropy of amphiphiles due to the formation of aggregates. Thus amphiphiles with longer chains entropically disfavor formation of aggregates making aggregate formation of these derivatives solely an enthalpy-driven process. This decrease in entropy may be explained by considering the effect of an amphiphile's cone angle on aggregate size. As tail length increases in a series of analogous amphiphiles, the cone angle decreases resulting in a higher aggregation number per aggregate. Formation of larger aggregates results in a larger decrease in entropy upon aggregate formation due to the greater number of amphiphiles per aggregate.

Figure 9:
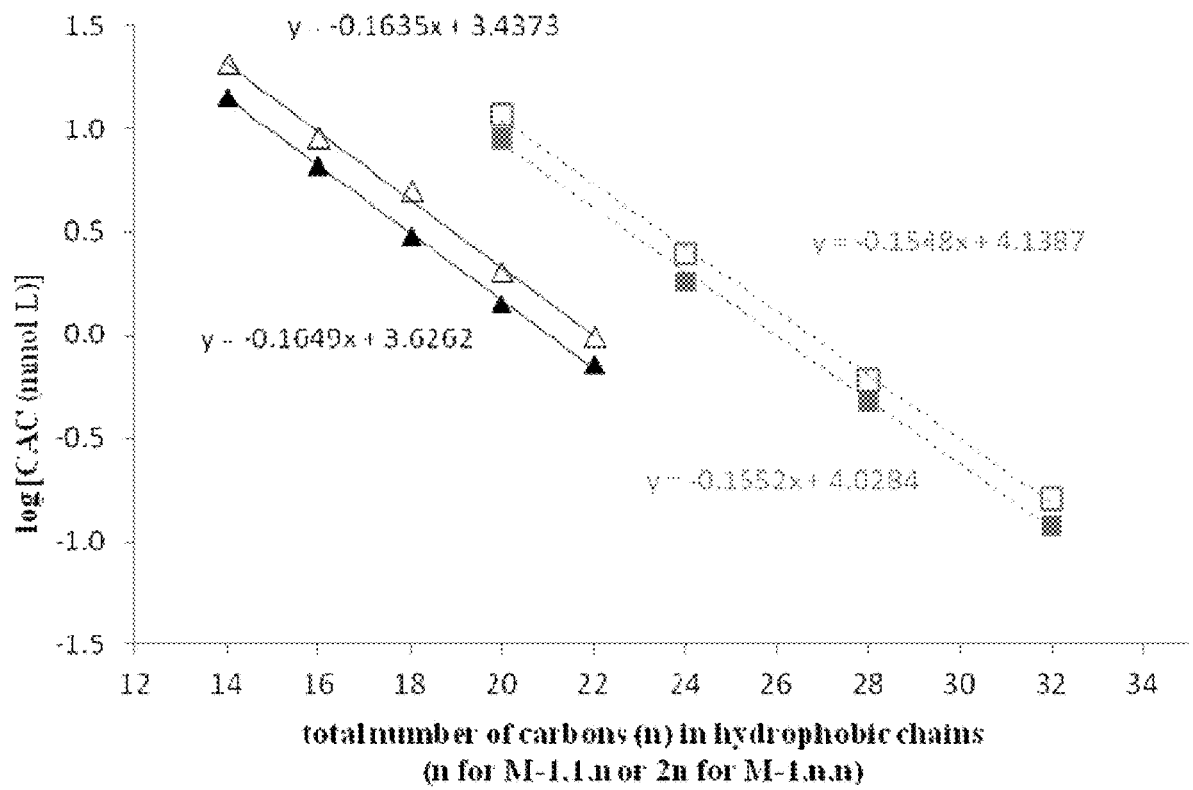
FIG. 9 is a graph which depicts a plot of log(CAC) versus tail length, comparing single-tailed and double-tailed compounds.
Figure 10:
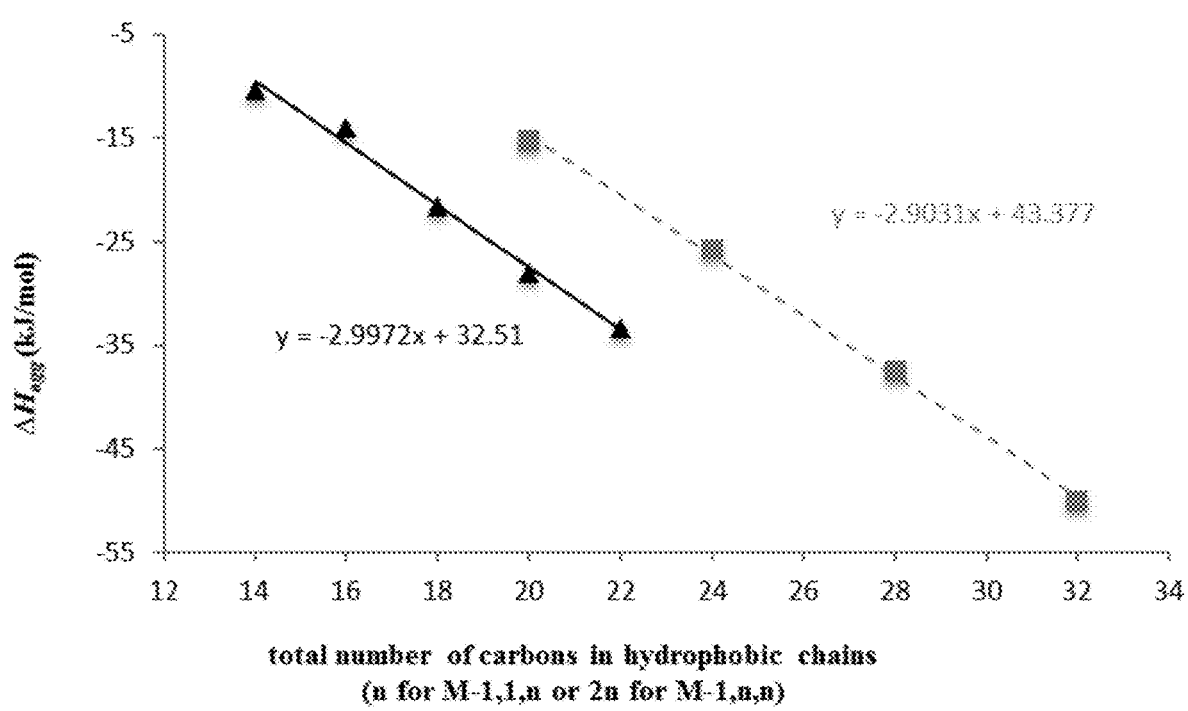
FIG. 10 is a graph which depicts a plot of $\Delta H_{agg}$ (kJ/mol) versus tail length, comparing single-tailed and double-tailed compounds.

FIG. 9 shows a plot of log(CAC) versus tail length for the single-tailed M-1,1,n series (▲) and double-tailed M-1 series (□). Closed data points refer to the CAC determined by conductivity while open data points (▲, □) refer to the CAC determined by ITC. FIG. 10 shows a plot of $\Delta$Hagg (kJ/mol) versus tail length for the single-tailed M-1,1,n series (▲) and double-tailed M-1 series (□).

Example 3

Minimum Inhibitory Concentration

The MIC values of all compounds from both double-tailed series were determined for four Gram-positive (*Staphylococcus aureus, Enterococcus faecalis, Streptococcus agalactiae*, and *Bacillus cereus*) and two Gram-negative (*Escherichia coli* and *Pseudomonas aeruginosa*) strains, which are shown in Table 3. MIC values of amphiphiles from the single-tailed M-1,1,n series are shown in Table 4.

TABLE 3

| | | Tail length (n for M-X, nn) | B. cereus (G+) | | E. faecalis (G+) | | S. agalactiae (G+) | | S. aureus (G+) | | E. coli (G−) | | P. aeruginosa (G−) | |
|---|---|---|---|---|---|---|---|---|---|---|---|---|---|---|
| M-P | M-1 | | M-P | M-1 | M-P | M-1 | M-P | M-1 | M-P | M-1 | M-P | M-1 | M-P | M-1 |
| 1 | 6 | 8,8 | >250 | >250 | >250 | >250 | >250 | >250 | >250 | >250 | >250 | >250 | >250 | >250 |
| 2 | 7 | 10,10 | 8 | 8 | 8 | 8 | 8 | 4 | 2 | 16 | 16 | 125 | 63 | >250 |
| 3 | 8 | 12,12 | 2 | 2 | 2 | 2 | 1 | 2 | 2 | 2 | 4 | 4-8 | 8 | 16 |
| 4 | 9 | 14,14 | 8 | 4 | 4 | 4 | 4 | 2-4 | 4 | 4-8 | 16 | 8 | 63 | 125 |
| 5 | 10 | 16,16 | 32 | 16 | 32 | 32 | 4 | 8 | 32 | 16 | 125 | 63 | >250 | >250 |

TABLE 4

| Compound | Tail length (n for $C_nH_{2n+1}$) | B. cereus (G+) | E. faecalis (G+) | S. agalactiae (G+) | S. aureus (G+) | E. coli (G−) | P. aeruginosa (G−) |
|---|---|---|---|---|---|---|---|
| S1 | 8 | >250 | >250 | >250 | >250 | >250 | >250 |
| S2 | 10 | 125 | 250 | 125 | >250 | >250 | >250 |
| S3 | 12 | 63 | 250 | 125 | 63 | >250 | >250 |
| S4 | 14 | 16 | 31 | 16 | 63 | 250 | >250 |
| S5 | 16 | 4 | 8 | 4 | 31 | 31 | >250 |
| S6 | 18 | 4 | 4 | 2 | 16 | 16 | 125 |
| S7 | 20 | 4 | 4 | 4 | 16 | 31 | 250 |
| S8 | 22 | >250 | >250 | >250 | >250 | 63 | >250 |

Figure 11:
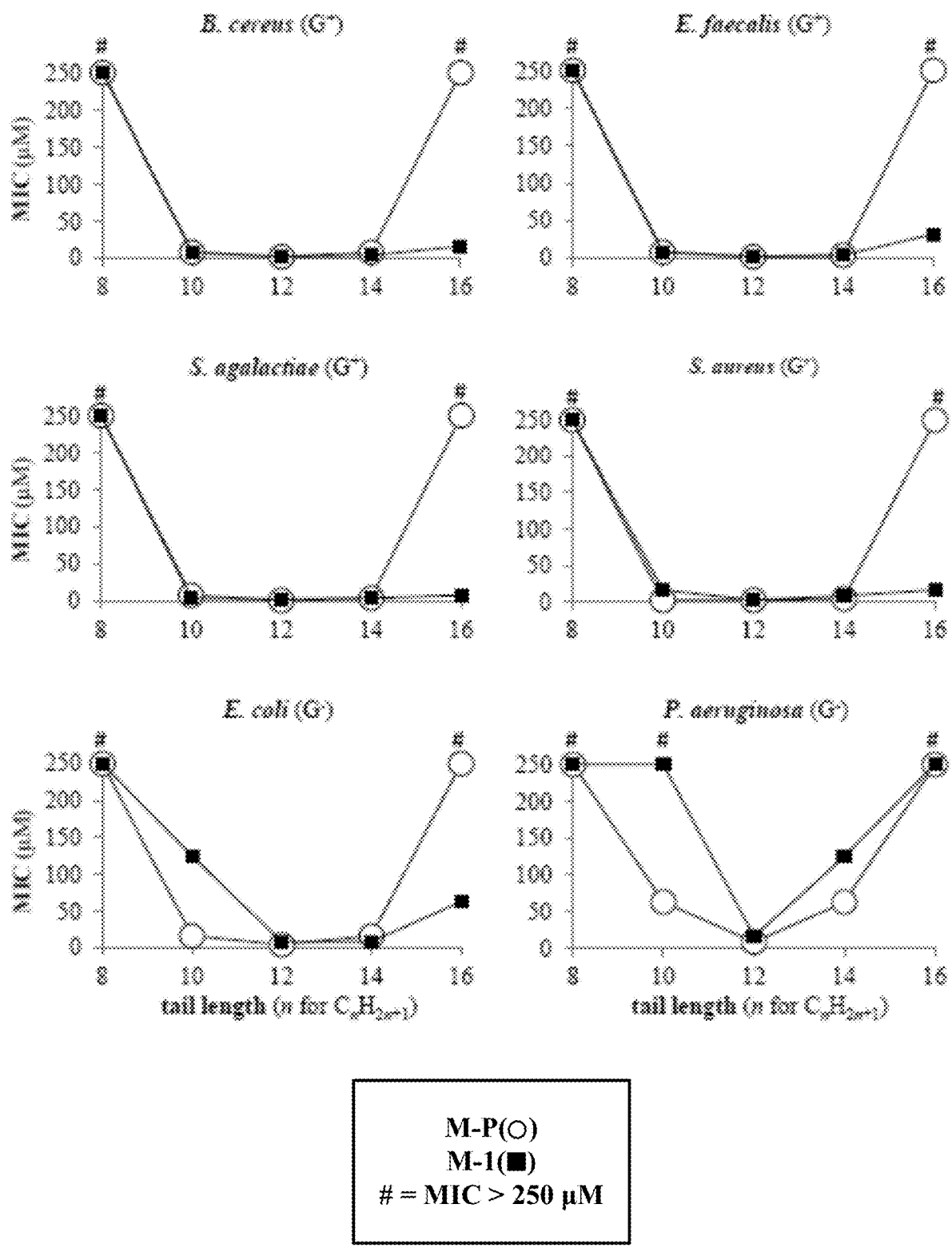
FIG. 11 is a series of graphs, each of which depicts a plot of log(CAC) versus tail length for double-tailed compounds tested against various bacterial species as indicated.

The effect of tail length and head group on log(MIC) is shown in FIG. 11. For both double-tailed series, the MIC decreases with tail length until an optimal tail length of 12 carbons per chain, above which the MIC increases. The derivatives with two 12-carbon chains, compounds 3 (M-P, 12,12) and 8 (M-1,12,12), have the lowest MIC values against each strain with values ranging from 1-2 μM for Gram-positive bacteria and 4-16 μM for Gram-negative bacteria. This trend is indicative of the relationship between solubility and bioactivity. Higher MIC values against Gram-negative strains may be due to their outer membrane, which is not present in Gram-positive bacteria.

Many antibacterial agents are ineffective against *P. aeruginosa* due to its semipermeable outer membrane and production of efflux pumps and β-lactamases. The contamination of medical equipment with *P. aeruginosa* biofilms contributes to hospital-acquired infections, particularly caused by antibiotic-resistant strains. While other antibacterial agents fail to inhibit *P. aeruginosa*, two amphiphiles tested, compounds 3 (M-P,12,12) and 8 (M-1,12,12), kill this organism at relatively low concentrations, which may prove highly useful in a healthcare setting. Notably, MIC values of compounds 3 (M-P,12,12) and 8 (M-1,12,12) against *P. aeruginosa*, 8 µM and 16 µM, respectively, are comparable to those of tobramycin at 6.4 µM, which is commonly used to treat infection in cystic fibrosis patients, and cefepime at 12.5 µM, an antispeduomonal cephalosporin.

MIC values between respective M-P and M-1 tail lengths were generally similar, indicating that replacing the trimethylammonium head group with a pyridinium did not significantly affect bioactivity. A notable exception is observed between the two derivatives with 16-carbon chains, where the trimethylammonium derivative compound 10, M-1,16,16, was more effective than the pyridinium derivative compound 5, M-P,16,16, for all strains except *P. aeruginosa*. For all tested compounds, the MBC was the same concentration or a two-fold concentration higher than the MIC, indicating the amphiphiles are bactericidal.

With only a few exceptions, MIC values for the double-tailed compounds were significantly below CAC values, demonstrating that amphiphile aggregation is not required to kill bacteria. At concentrations near or above the CAC, the amphiphile may act as a detergent, solubilizing the cell membrane—a mechanism of action that could be detrimental to prokaryotic cells. Amphiphiles at sub-CAC levels are potent antibacterials at concentrations where detergent effects are not observed. It is recognized that CAC values reported here, measured in pure water, may differ to some degree from the CAC values in the medium used for MIC studies.

Figure 12:
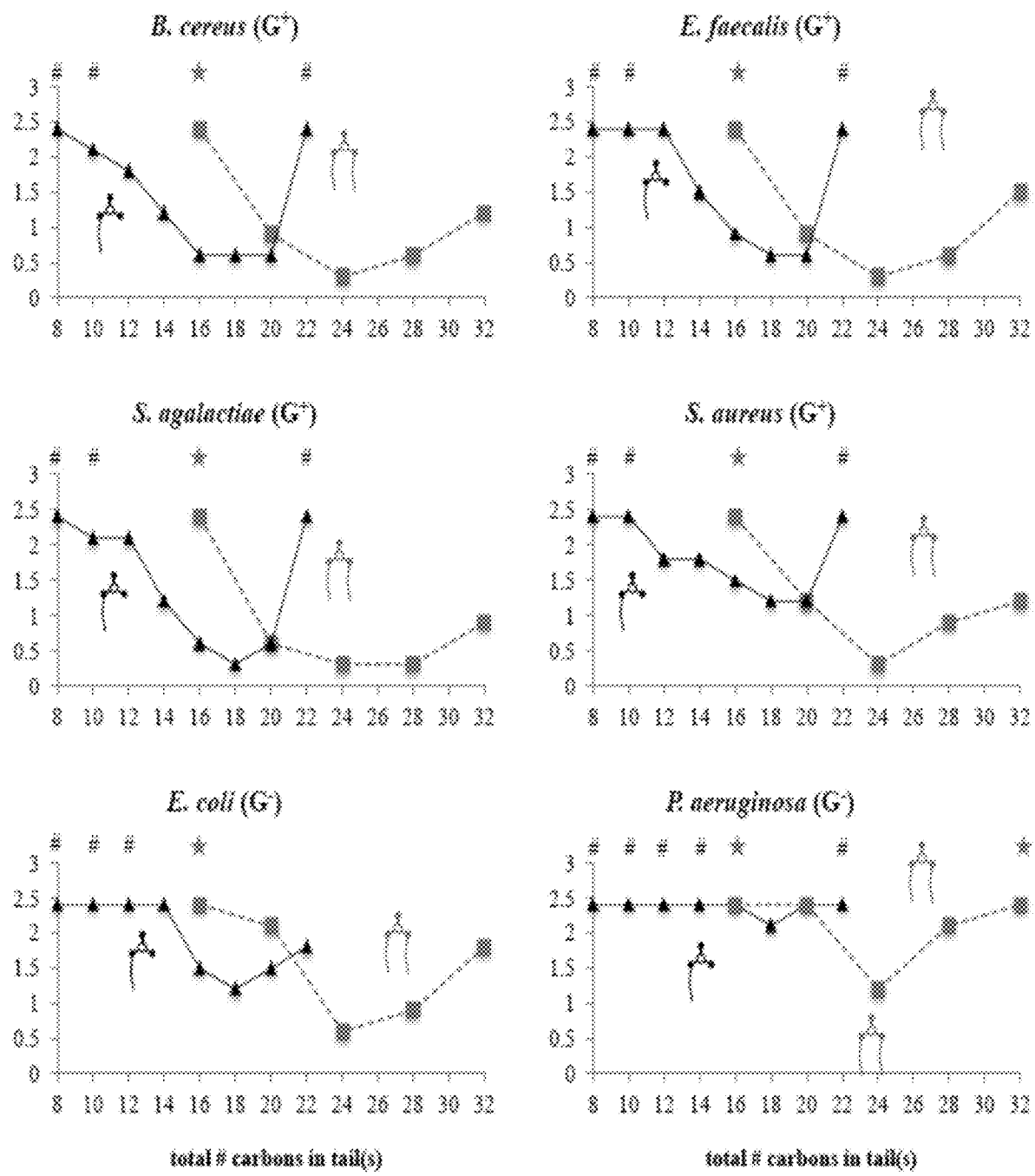
FIG. 12 is a series of graphs, each of which depicts a plot of log(CAC) versus tail length comparing single-tailed and double-tailed compounds tested against various bacterial species as indicated.

FIG. 12 shows the effect of total number of hydrocarbon groups in the alkyl chain on the MIC values for the single-tailed M-1,1,n series (▲) and double-tailed M-1 series (■), where #=MIC>250 µM. G$^+$=Gram-positive; G$^-$=Gram-negative.

Example 4

Synergistic Combinations

Figure 13:
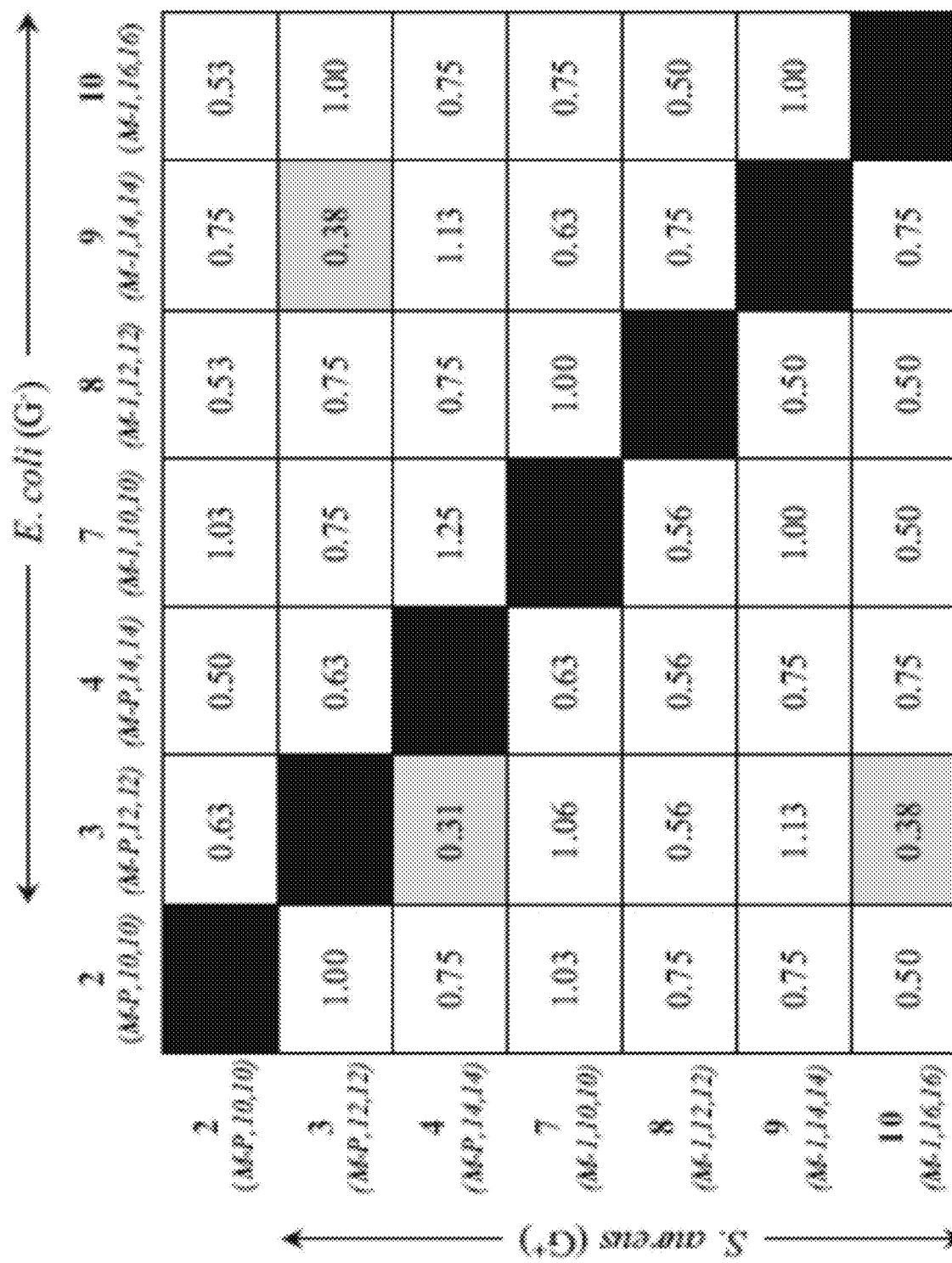
FIG. 13 is a chart which depicts the fractional inhibitory concentration ("FIC") results for a synergy study of various combinations of inventive double-tailed compounds.

Synergy studies for double-tailed M-P and M-1 amphiphiles tested against *E. coli* and *S. aureus* are shown in FIG. 13. The FIC value for each combination is given. Shaded blocks indicate synergistic combinations (FIC<0.5). Numbers below the diagonal represent FIC values against *S. aureus*. Numbers above the diagonal represent FIC values against *E. coli*. In addition to determining the antibacterial activity of individual amphiphiles, combination studies were performed in order to determine if binary mixtures of amphiphiles demonstrate synergy in killing representative Gram-positive (*S. aureus*) and Gram-negative (*E. coli*) organisms. A combination is considered synergistic if a mixture of amphiphiles has greater antimicrobial activity than simply an additive effect. The fractional inhibitory concentration (FIC) was used to indicate whether two chemicals were synergistic (FIC<0.5), indifferent (FIC 0.5-4.0), or antagonistic (FIC>4.0). As shown in FIG. 13, two amphiphile combinations are synergistic against *S. aureus*: combinations of compounds 3 and 4 (FIC=0.31) and compounds 3 and 10 (FIC=0.38). In addition, one combination is synergistic against *E. coli*: compound 3 and 9 (FIC=0.38). All three synergistic combinations contain compound 3 (M-P,12,12). The use of synergistic antibacterial combinations is expected to be beneficial in a health-care setting, where frequent antimicrobial use has contributed to the presence of antibiotic-resistant organisms.

Figure 14:
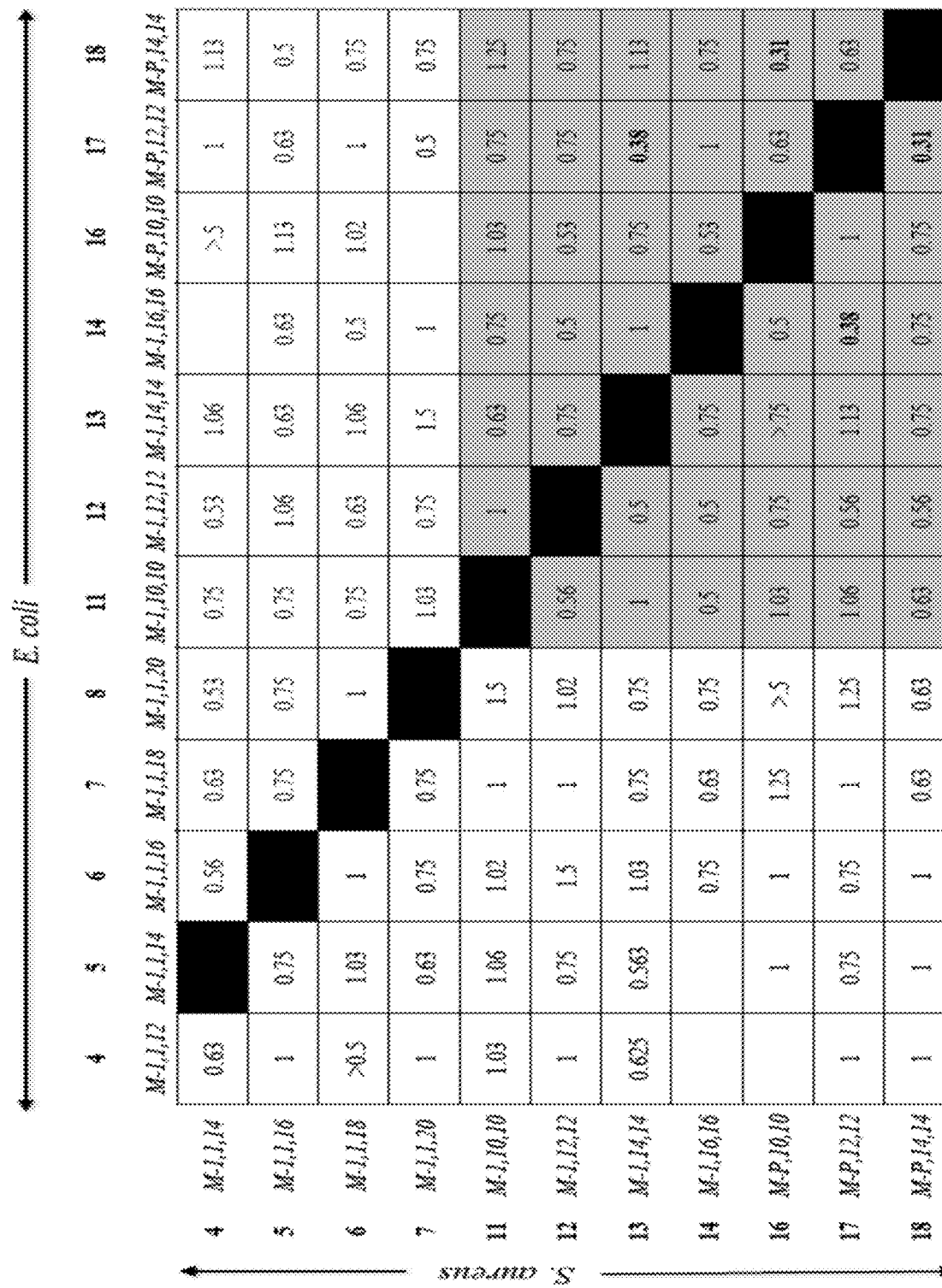
FIG. 14 is a chart which depicts the fractional inhibitory concentration ("FIC") results for a synergy study of various combinations of inventive single-tailed and double-tailed compounds.

Synergy studies for M-P; M-1; and M-1,1,n amphiphiles tested against *E. coli* and *S. aureus* are shown in FIG. 14. The FIC value for each combination is given. Bolded FIC values indicate synergistic combinations (FIC<0.5). Numbers below the black diagonal represent FIC values against *S. aureus*. Numbers above the diagonal represent FIC values against *E. coli*.

Example 5

Synthesis of Intermediates 11 and 12
Compound 11 (M-P)

1,3,5-tribromomethylbenezene (1.0 g, 2.8 mmol, Sigma-Aldrich) was dissolved in acetone (200 mL) at room temperature in a round bottom flask. The solution was equipped with a stir-bar and attached to an addition funnel. Pyridine (0.45 mL, 5.6 mmol, Sigma-Aldrich) was dissolved in acetone (100 mL) and added drop-wise to the stirring solution of 1,3,5-tribromethylbenzene at room temperature and allowed to react overnight. A white precipitate formed. The crude reaction mixture was vacuum filtered, washed with acetone, and dried under vacuum yielding 943 mg (77%) of a tan solid, 11.

Analytical data for compound 11: mp=223.9-226.8° C. (dec). $^1$H NMR (DMSO-d$_6$, 300 MHz, 25° C.) δ: 9.22 (d, 2H, Pyr-H), 8.66 (t, 1H, Pyr-H), 8.22 (t, 2H, Pyr-H), 7.56 (s, 1H, ArH), 7.54 (s, 2H, ArH), 5.89 (s, 2H, ArCH$_2$N), 4.69 (s, 4H, ArCH$_2$Br). $^{13}$C NMR (DMSO-d$_6$, 75 MHz, 25° C.) δ: 146.6, 145.4, 141.0, 135.8, 131.3, 129.8, 129.1, 63.0, 33.7.

Compound 12 (M-1)

1,3,5-tribromomethylbenezene (2.01 g, 5.6 mmol) was dissolved in acetone (400 mL) at room temperature in a round bottom flask. The solution was cooled on an ice bath for 30 minutes, equipped with a stir-bar, and attached to an addition funnel. An ethanolic trimethylamine solution (1.6 mL, 6.7 mmol, ACROS) was diluted with acetone (200 mL) and cooled on an ice bath for 30 minutes. The trimethylamine solution was added drop-wise to the stirring solution of 1,3,5-tribromethylbenzene. The reaction was run overnight, and allowed to warm slowly to room temperature. A white precipitate containing a mixture of 12 and a biscationic side product formed. The crude reaction mixture was briefly heated to 50° C. and vacuum filtered. The mother liquor (which contained a mixture of 12 and unreacted starting material) was transferred to a clean RBF and the solvent was removed by rotary evaporation. The resulting solid was resuspended in room temperature acetone for 30 minutes, vacuum filtered, and dried under vacuum yielding 12 (white solid).

The solid filtered from the crude reaction mixture was resuspended in a solution of acetone and ethanol (100:3), heated to 60° C., stirred for at least 30 minutes, and vacuum filtered. The filtrate was transferred to a clean flask and the solvent was removed by rotary evaporation yielding additional 20 (white solid, total yield=860 mg, 37%).

Analytical data for compound 12: mp=204.5-207.9° C. $^1$H NMR (DMSO-d$_6$, 400 MHz, 25° C.) δ: 7.70 (s, 1H, ArH); 7.56 (s, 2H, ArH); 4.76 (s, 4H, ArCH$_2$N); 4.56 (s, 2H, ArCH$_2$Br); 3.03 (s, 9H, N(CH$_3$)$_3$). $^{13}$C NMR (DMSO-d$_6$, 100 MHz, 25° C.) δ: 139.4, 133.4, 131.6, 129.4, 67.0, 51.8, 33.2.

Example 6

Synthesis of Specific Compounds
General Protocol A

Compound 11 or 12 was added to a two-neck round bottom flask and dissolved in ethanol. The flask was equipped with a stir bar and attached to a water-cooled condenser. Excess dimethylalkylamine (NMe$_2$(CH$_2$)$_{n-1}$CH$_3$, where n=8, 10, 12, 14 or 16) was added slowly to the flask via syringe. The reaction was heated to reflux and allowed react overnight. Volatile materials were removed under a flow of N$_2$ (g).

The resulting crude solid was resuspended in acetone to dissolve any residual dimethylalkylamine and vacuum filtered to yield the solid amphiphile product (1-10).

Compound (1) M-P,8,8

The product was synthesized via general protocol A. Compound 11 (2.900 g, 6.660 mmol) was dissolved in ethanol (50 mL) and reacted with N,N-dimethyoctylamine (ACROS, 97%, 2.74 mL, 13.3 mmol). Reaction yielded 4.40 g (88%) of a tan solid, mp=147.3-154.0° C. (dec). $^1$H NMR (DMSO-d$_6$, 400 MHz, 25° C.) S: 9.36 (d, 2H, Pyr-H), 8.66 (t, 1H, Pyr-H), 8.199 (t, 2H, Pyr-H), 7.89 (s, 2H, ArH), 7.87 (s, 1H, ArH), 6.09 (s, 2H, ArCH$_2$), 4.62 (s, 4H, ArCH$_2$), 3.03 (s, 12H, NCH$_3$), 1.77 (s, 4H, NCH$_2$CH$_2$), 1.162-1.377 (m, 20H), 0.869 (t, 6H, CH$_2$CH$_3$). $^{13}$C NMR (DMSO-d$_6$, 100 MHz, 25° C.) δ: 146.13, 145.22, 138.0, 135.19, 135.08, 129.7, 128.3, 65.3, 63.7, 62.3, 49.1, 31.2, 28.55, 28.50, 25.9, 22.1, 21.9, 14.0. TOF-HRMS calculated for [M-Br]$^+$: 668.31539, 669.31875, 670.31335, 671.31671, 672.3113, 673.31466; observed (ppm error): 668.31389 (−2.24), 669.31624 (−3.75), 670.31269 (−0.98), 671.31494 (−2.64), 672.31114 (−0.24), 673.31301 (−2.47).

Compound (2) M-P,10,10

The product was synthesized via general protocol A. Compound 11 (1.200 g, 0.275 mmol) was dissolved in ethanol (50 mL) and reacted with N,N-dimethyldecylamine (TCI, >93%, 1.24 mL, 0.61 mmol). Reaction yielded 1.40 g (63% yield) of an off-white solid, mp=171.4-182.0° C. (dec). $^1$H NMR (DMSO-d$_6$, 400 MHz, 25° C.) δ: 9.30 (d, 2H, Pyr-H), 8.67 (t, 1H, Pyr-H), 8.21 (t, 2H, Pyr-H), 7.85 (s, 2H, ArH),7.81 (s, 1H, ArH), 6.05 (s, 2H, ArCH$_2$), 4.58 (s, 4H, ArCH$_2$), 3.00 (s, 12H, NCH$_3$), 1.77 (s, 4H, NCH$_2$CH$_2$), 1.135-1.387 (m, 28H), 0.865 (t, 6H, CH$_2$CH$_3$). $^{13}$C NMR (DMSO-d$_6$, 100 MHz, 25° C.) δ: 146.1, 145.2, 138.0, 135.20, 135.08, 129.7, 128.3, 65.3, 63.6, 62.2, 49.1, 31.3, 28.95, 28.88, 28.69, 28.61, 25.9, 22.1, 21.9, 14.0. TOF-HRMS calculated for [M-Br]$^+$: 724.37799, 725.38135, 726.37595, 727.37931, 728.3739, 729.37726; observed (ppm error): 724.37664 (−1.86), 725.37872 (−3.63), 726.37556 (−0.54), 727.37767 (−2.25), 728.37415 (+0.34), 729.37582 (−1.97).

Compound (3) M-P,12,12

The product was synthesized via general protocol A. Compound 11 (0.250 g, 0.573 mmol) was dissolved in ethanol (5 mL) and reacted with N,N-dimethyldodecylamine (MP Biomedicals, 0.34 mL, 1.26 mmol). Reaction yielded 0.383 g (77% yield) of an off-white solid, mp=192.2-195.7° C. (dec). $^1$H NMR (DMSO-d$_6$, 400 MHz, 25° C.) δ: 9.34 (d, 2H, Pyr-H), 8.67 (t, 1H, Pyr-H), 8.20 (t, 2H, Pyr-H), 7.87 (s, 2H, ArH), 7.83 (s, 1H, ArH), 6.07 (s, 2H, ArCH$_2$), 4.60 (s, 4H, ArCH$_2$), 3.02 (s, 12H, NCH$_3$), 1.76 (s, 4H, NCH$_2$CH$_2$), 1.15-1.39 (m, 36H), 0.854 (t, 6H, CH$_2$CH$_3$). $^{13}$C NMR (DMSO-d$_6$, 75 MHz, 25° C.) δ: 146.1, 145.2, 138.0, 135.20, 135.07, 129.7, 128.3, 65.3, 63.6, 62.2, 49.1, 31.3, 29.05, 29.02, 29.00, 28.9, 28.72, 28.61, 25.9, 22.1, 21.9, 13.9. TOF-HRMS calculated for [M-Br]$^+$: 780.44059, 781.44395, 782.43855, 783.44191, 784.4365, 785.43986; observed (ppm error): 780.43869 (−2.43), 781.44113 (−3.61), 782.43773 (−1.05), 783.44003 (−2.40), 784.43661 (+0.14), 785.43813 (−2.20).

Compound (4) M-P,14,14

The product was synthesized via general protocol A. Compound 11 (0.500 g, 1.150 mmol) was dissolved in ethanol (5 mL) and reacted with N,N-dimethyltetradecylamine (Aldrich, 95%, 0.77 mL, 2.52 mmol). Reaction yielded 0.920 g (87% yield) of an off-white solid, mp=201.5-213.0° C. (dec). $^1$H NMR (DMSO-d$_6$, 400 MHz, 25° C.) δ: 9.23 (d, 2H, Pyr-H), 8.68 (t, 1H, Pyr-H), 8.21 (t, 2H, Pyr-H), 7.8 (s, 2H, ArH), 7.75 (s, 1H, ArH), 6.01 (s, 2H, ArCH$_2$), 4.55 (s, 4H, ArCH$_2$), 2.98 (s, 12H, NCH$_3$), 1.76 (s, 4H, NCH$_2$CH$_2$), 1.17-1.35 (m, 44H), 0.856 (t, 6H, CH$_2$CH$_3$). $^{13}$C NMR (DMSO-d$_6$, 100 MHz, 25° C.) δ: 146.1, 145.2, 138.0, 135.21, 135.08, 129.7, 128.3, 65.3, 63.5, 62.2, 49.1, 31.3, 29.08, 29.02, 28.90, 28.7, 26.6, 25.9, 22.1, 21.9, 13.9. TOF-HRMS calculated for [M-Br]$^+$: 836.50319, 837.50655, 838.50115, 839.50451, 840.4991, 841.50246; observed (ppm error): 836.50151 (−2.01), 837.50395 (−3.10), 838.50078 (−0.44), 839.50309 (−1.69), 840.49985 (+0.89), 841.50132 (−1.35).

Compound (5) M-P,16,16

The product was synthesized via general protocol A. Compound 11 (0.250 g, 0.573 mmol) was dissolved in ethanol (5 mL) and reacted with N,N-dimethylhexadecylamine (TCI, 98%, 0.42 mL, 1.26 mmol). Reaction yielded 0.512 g (92% yield) of an off-white solid, mp=197.7-216.6° C. (dec). $^1$H NMR (DMSO-d$_6$, 400 MHz, 25° C.) δ: 9.32 (d, 2H, Pyr-H), 8.67 (t, 1H, Pyr-H), 8.20 (t, 2H, Pyr-H), 7.86 (s, 2H, ArH), 7.81 (s, 1H, ArH), 6.06 (s, 2H, ArCH$_2$), 4.60 (s, 4H, ArCH$_2$), 3.01 (s, 12H, NCH$_3$), 1.76 (s, 4H, NCH$_2$CH$_2$), 1.10-1.36 (m, 52H), 0.851 (t, 6H, CH$_2$CH$_3$). $^{13}$C NMR (DMSO-d$_6$, 75 MHz, 25° C.) δ: 146.1, 145.2, 138.0, 135.20, 135.07, 129.7, 128.3, 65.4, 63.5, 62.2, 49.1, 31.3, 29.06, 29.00, 28.90, 28.69, 28.62, 25.9, 22.1, 21.9, 13.9. TOF-HRMS calculated for [M-Br]$^+$: 892.56579, 893.56915, 894.56375, 895.56711, 896.56170, 897.56506; observed (ppm error): 892.56381 (−2.22), 893.56636 (−3.12), 894.56319 (−0.63), 895.56533 (−1.99), 896.56233 (+0.70), 897.56359 (−1.64).

Compound (6) M-1,8,8

The product was synthesized via general protocol A. Compound 12 (502 mg, 1.20 mmol) was dissolved in ethanol (30 mL) and reacted with N,N-dimethyoctylamine (ACROS, 97%, 0.67 mL, 3.00 mmol). Reaction yielded 150 mg (20% yield) of a white solid, mp=182.2-186.3° C. (dec). $^1$H NMR (DMSO-d$_6$, 400 MHz, 25° C.) δ: 7.86 (s, 1H, Ar H); 7.83 (s, 2H, ArH); 4.62 (s, 2H, ArCH$_2$); 4.59 (s, 4H, ArC H$_2$); 3.11 (s, 9H, N(CH$_3$)$_3$); 3.02 (s, 12H, N(CH$_3$)$_2$); 1.80 (m, 4H, NCH$_2$CH$_2$); 1.20-1.39 (m, 20H); 0.88 (t, 6H, CH$_2$C H$_3$). $^{13}$C NMR (DMSO-d$_6$, 100 MHz, 25° C.) δ: 139.0, 138.8, 129.7, 129.5, 66.8, 65.4, 63.4, 51.8, 49.1, 31.2, 28.6, 22.9, 22.1, 21.9, 14.0. TOF-HRMS calculated for [M-Br]$^+$: 648.34669, 649.35005, 650.34465, 651.34801, 652.34260, 653.34596; observed (ppm error): 648.34571 (−1.51), 649.34765 (−3.70), 650.34425 (−0.62), 651.34629 (−2.64), 652.34275 (+0.23), 653.34528 (−1.04).

Compound (7) M-1,10,10

The product was synthesized via general protocol A. Compound 12 (100 mg, 0.30 mmol) was dissolved in ethanol (15 mL) and reacted with N,N-dimethyldecylamine (TCI, >93%, 150 mg, 0.75 mmol). Reaction yielded 156 mg (66% yield) of a white solid, mp=189.6-191.8° C. (dec). $^1$H NMR (DMSO-d$_6$, 400 MHz, 25° C.) δ: 7.85 (s, 1H, ArH); 7.82 (s, 2H, ArH); 4.61 (s, 2H, ArCH$_2$); 4.59 (s, 4H, ArCH$_2$); 3.10 (s, 9H, N(CH$_3$)$_3$); 3.02 (s, 12H, N(CH$_3$)$_2$); 1.80 (m, 4H, NCH$_3$CH$_2$); 1.18-1.39 (m, 28H); 0.86 (t, 6H, CH$_2$CH$_3$). $^{13}$C NMR (DMSO-d$_6$, 100 MHz, 25° C.) δ:139.0, 138.8, 129.7, 129.5, 66.9, 65.4, 51.8, 49.1, 31.3, 28.94, 28.91, 28.69, 28.61, 25.9, 22.1, 21.9, 14.0. TOF-HRMS calculated for

[M-Br]$^+$: 704.40929, 705.41265, 706.40725, 707.41061, 708.40520, 709.40856; observed (ppm error): 704.40814 (−1.63), 705.41038 (−3.22), 706.40666 (−0.84), 707.40881 (−2.54), 708.40556 (+0.51), 709.40788 (−0.96).

Compound (8) M-1,12,12

The product was synthesized via general protocol A. Compound 12 (105 mg, 0.30 mmol) was dissolved in ethanol (15 mL) and reacted with N,N-dimethydodecylamine (M Biomedicals, 170 mg, 0.75 mmol). Reaction yielded 160 mg (63% yield) of a white solid, mp=202.9-204.2° C. (dec). $^1$H NMR (DMSO-d$_6$, 400 MHz, 25° C.) δ: 7.84 (s, 1H, ArH); 7.81 (s, 2H, ArH); 4.61 (s, 2H, ArCH$_2$); 4.59 (s, 4H, ArCH$_2$); 3.10 (s, 9H, N(CH$_3$)$_3$); 3.01 (s, 12H, N(CH$_3$)$_2$); 1.80 (m, 4H, NCH$_3$CH$_2$); 1.16-1.40 (m, 36H); 0.86 (t, 6H, CH$_2$CH$_3$). $^{13}$C NMR (DMSO-d$_6$, 100 MHz, 25° C.) δ: 139.0, 138.8, 129.7, 129.5, 66.9, 65.4, 63.5, 51.8, 49.1, 31.3, 29.06, 29.02, 28.99, 28.92, 28.73, 28.62, 25.9, 22.1, 21.9, 14.0. TOF-HRMS calculated for [M-Br]$^+$: 760.47189, 761.47525, 762.46985, 763.47321, 764.46780, 765.47116; observed (ppm error): 760.47027 (−2.13), 761.47219 (−4.02), 762.46895 (−1.18), 763.47087 (−3.06), 764.46784 (+0.05), 765.47061 (−0.72).

Compound (9) M-1,14,14

The product was synthesized via general protocol A. Compound 12 (105 mg, 0.30 mmol) was dissolved in ethanol (15 mL) and reacted with N,N-dimethytetradecylamine (Aldrich, 95%, 195 mg, 0.75 mmol). Reaction yielded 202 mg (75% yield) of a white solid, mp=207.0-212.4° C. (dec). $^1$H NMR (DMSO-d$_6$, 400 MHz, 25° C.) δ: 7.83 (s, 1H, Ar—H); 7.81 (s, 2H, Ar—H); 4.61 (s, 2H, Ar—CH$_2$); 4.58 (s, 4H, Ar—CH$_2$); 3.10 (s, 9H, N—(CH$_3$)$_3$); 3.01 (s, 12H, N—(CH$_3$)$_2$); 1.79 (m, 4H, NCH$_3$CH$_2$); 1.17-1.38 (m, 44H); 0.85 (t, 6H, CH$_2$CH$_3$). $^{13}$C NMR (DMSO-d$_6$, 100 MHz, 25° C.) δ: 139.0, 138.8, 129.7, 129.5, 66.9, 65.4, 63.4, 51.8, 49.1, 31.3, 29.08, 29.03, 28.93, 28.72, 28.63, 25.9, 22.1, 21.9, 14.0. TOF-HRMS calculated for [M-Br]$^+$: 816.53449, 817.53785, 818.53245, 819.53581, 820.53040, 821.53376; observed (ppm error): 816.53302 (−1.80), 817.53483 (−3.69), 818.53172 (−0.89), 819.53363 (−2.66), 820.53097 (+0.69), 821.53291 (−1.03).

Compound (10) M-1,16,16

The product was synthesized via general protocol A. Compound 12 (100 mg, 0.30 mmol) was dissolved in ethanol (15 mL) and reacted with N,N-dimethyhexadecylamine (TCI, 98%, 200 mg, 0.75 mmol). Reaction yielded 170 mg (60% yield) of a white solid, mp=209.3-211.1° C. (dec). H NMR (DMSO-d$_6$, 400 MHz, 25° C.) δ: 7.83 (s, 1H, ArH); 7.80 (s, 2H, ArH); 4.60 (s, 2H, ArCH$_2$); 4.58 (s, 4H, ArCH$_2$); 3.09 (s, 9H, N(CH$_3$)$_3$); 3.00 (s, 12H, N(CH$_3$)$_2$); 1.80 (m, 4H, NCH$_3$CH$_2$); 1.20-1.39 (m, 52H); 0.85 (t, 6H, CH$_2$CH$_3$). $^{13}$C NMR (DMSO-d$_6$, 100 MHz, 25° C.) δ: 139.0, 138.8, 129.7, 129.5, 66.9, 65.4, 63.4, 51.8, 49.1, 31.3, 29.08, 29.02, 28.94, 28.7, 28.6, 26.0, 22.1, 21.9, 14.0. TOF-HRMS calculated for [M-Br]$^+$: 872.59709, 873.60045, 874.59505, 875.59841, 876.59300, 877.59636; observed (ppm error): 872.59603 (−1.21), 873.59814 (−2.64), 874.59478 (−0.31), 875.59683 (−1.80), 876.59423 (+1.40), 877.59591 (−0.51).

Example 7

General Laboratory Methods
Synthesis and Analysis

All solvents and reagents were used as received from the indicated chemical supplier unless otherwise specified. Melting points for solids were measured using a Mel-Temp apparatus with a digital thermometer (uncorrected). Nuclear magnetic resonance spectra were collected using one of the following instruments, as noted: Bruker-Spectrospin 400 ($^1$H: 400 MHz, $^{13}$C: 100 MHz) or Bruker-Spectrospin 300 ($^1$H: 300 MHz, $^{13}$C: 75 MHz). NMR Spectra were analyzed using Bruker TopSpin software, version 3.2. The solvent residual peak was used as a reference. $^{13}$C NMR peaks are reported to one place, unless signals differ by <0.15 ppm, in which case peaks are reported to two places. Exact mass measurements were obtained in flow injection experiments on a 6224 time of flight mass spectrometer (TOF-MS) (Agilent Technologies, Santa Clara, Calif.). Compounds were ionized by positive ion electrospray (ESI) under the following conditions: capillary voltage, +2500V, nozzle voltage, 500 V; fragmentor voltage, 175 V; drying gas temperature, 325° C.; drying gas flow, 5 L/min; nebulizer, 40 psi. MS data was collected in full scan mode (500 ms/scan) over the range of 100-1700 m/z. Mass errors were less than 5 ppm for all observed compounds. Mass resolving power, m/Δm, was ~19,000 at 922 m/z. Mass Hunter software version B.04 was used for all data acquisition and analysis.

Isothermal Titration Calorimetry

CAC and ΔH$_{agg}$ were determined using a Nano-ITC (TA-Instruments). Prior to each experiment the sample cell was washed with dH$_2$O (300 mL), ethanol (100 mL), dH$_2$O (300 mL) and nanopure water (200 mL). Next, 950 μL of nanopure water was added to the sample cell. A concentrated aqueous solution (>>CAC) of amphiphile was prepared and equilibrated at 37° C. A 250 μL syringe was filled with the aqueous solution, and loaded into the Nano ITC. Multiple single injections in aliquots of 5 μL were injected into the sample cell with time intervals varying from 300 s to 1400 s. Samples were continuously stirred (300 rpm) throughout the titration. The Nano-Analyze program (TA-Instruments) was used to analyze the data. CAC and ΔH$_{agg}$ values reported are the average of two or more repeat experiments for each amphiphile.

Bacterial Strains and Growth Conditions

The Gram-positive bacterial strains used tested were Staphylococcus aureus subsp. aureus ATCC® 29213™, Enterococcus faecalis ATCC® 29212™, Bacillus cereus, and Streptococcus agalactiae J48.[58] The Gram-negative bacterial strains used were Escherichia coli ATCC® 25922™ and Pseudomonas aeruginosa ATCC® 27853™. All strains were grown in 1× Mueller-Hinton Broth at 37° C. for 12-24 h. For the MIC and combination studies, bacterial suspensions were prepared by diluting overnight cultures to 5×10$^6$ CFU/mL in 2× Mueller-Hinton Broth, so that when amphiphile solutions are added the final broth strength is 1×.

Minimum Inhibitory Concentration and Minimum Bactericidal Concentration

The methods used to determine the MIC and MBC were performed as previously described and followed the standards set forth by the Clinical and Laboratory Standards Institute (See Ladow, J. E.; Warnock, D. C.; Hamill, K. M.; Simmons, K. L.; Davis, R. W.; Schwantes, C. R.; Flaherty, D. C.; Willcox, J. A. L.; Wilson-Henjum, K.; Caran, K. L.; Minbiole, K. P. C.; Seifert, K. Bicephalic amphiphile architecture affects antibacterial activity. Eur. J. Med. Chem. 2011, 46, 4219-4226 and P. A. Wayne Methods for dilution antimicrobial tests for bacteria that grow aerobically. 2009.). Briefly, compounds were serially diluted and 100 μL of each dilution were added to the wells of a 96-well flat-bottomed microtiter plate in triplicate. After adding 100 μL of the bacterial cell suspension, the plates were incubated at 37° C. for 72 h. The MIC of the compound was defined as the minimum concentration that resulted in visible inhibition of bacterial growth. In order to determine the MBC, a 100 μl aliquot from each triplicate well was grown on Todd-Hewitt agar and incubated for 24 h at 37° C. The MBC was defined as the concentration of the compound that resulted in a 99.9% reduction of the bacterial CFU/mL. The MIC was considered to be bactericidal if the MBC was the same concentration or one concentration higher in the dilution series as the MIC, per Motyl, M.; Dorso, K.; Barrett, J.; Giacobbe, R. Basic microbiological techniques used in antibacterial drug discovery. *Curr. Protoc. Pharmacol.* 2006, Chapter 13.

Combination Studies

To determine if two amphiphiles act synergistically to kill *E. coli* or *S. aureus*, combination studies were performed using the checkerboard technique as described in Giacometti, A.; Cirioni, O.; Del Prete, M. S.; Paggi, A. M.; D'Errico, M. M.; Scalise, G. Combination studies between polycationic peptides and clinically used antibiotics against Gram-positive and Gram-negative bacteria. Peptides. 2000, 21, 1155-1160. Amphiphiles with MIC values higher than the maximum concentration used (>250 μM) were excluded from the combination studies. The amphiphile concentrations used in the combination studies ranged from 1/16 to 2× the MIC. Fifty microliters of each amphiphile dilution and 100 μL of the bacterial suspension were added to the wells of a 96-well flat-bottomed microtiter plate. Control wells consisted of the bacterial suspension treated with media alone and bacteria treated with individual amphiphiles. Plates were incubated at 37° C. for 72 h. The FIC index was calculated using the following formula: $FIC=FIC_A+FIC_B=A/MIC_A+B/MIC_B$. A and B are the MIC values of compound A and compound B when combined, and $MIC_A$ and $MIC_B$ are the MIC of compound A and B alone. A combination was considered to be synergistic if the FIC was less than 0.5; a combination was considered indifferent with an FIC of 0.5-4; and a combination was considered antagonistic with an FIC>4. The FIC indices of synergistic combinations were confirmed in two separate experiments.

REFERENCES

The following literature references are believed to useful to an understanding of the inventive subject matter in the context of its place in the relevant art. Citation here is not to be construed as an assertion or admission that any reference cited is material to patentability of the inventive subject matter. Applicants will properly disclose information material to patentability in an Information Disclosure Statement. Each of the following documents is hereby incorporated by reference in its entirety in this application:

Fan, F. F. Defining and Combating the Mechanisms of Triclosan Resistance in Clinical Isolates of *Staphylococcus aureus*. Antimicrob. Agents Chemother. 2002, 46, 3343-3347.

Chea, P. Executive summary: Select findings, conclusions, and policy recommendations. Clinical Infectious Diseases. 2005, 41, S224-S227.

Gilbert, M.; MacDonald, J.; Louie, M.; Gregson, D.; Zhang, K.; Elsayed, S.; Laupland, K.; Nielsen, D.; Wheeler, V.; Lye, T.; Conly, J. Prevalence of USA300 colonization or infection and associated variables during an outbreak of community-associated methicillin-resistant *Staphylococcus aureus* in a marginalized urban population. Canadian Journal of Infectious Diseases and Medical Microbiology. 2007, 18, 357-362.

Okeke, I. N.; Lamikanra, A.; Edelman, R. Socioeconomic and behavioral factors leading to acquired bacterial resistance to antibiotics in developing countries. Emerging Infectious Diseases. 1999, 5, 18-27.

Taubes, G. The bacteria fight back. Science. 2008, 321, 356-360+361.

Scheffler, R. J.; Colmer, S.; Tynan, H.; Demain, A. L.; Gullo, V. P. Antimicrobials, drug discovery, and genome mining. Appl. Microbiol. Biotechnol. 2013, 97, 969-978.

World Helath Organization, Evolving threat of antimicrobial resistance. *Who. Drug. Inf.* 2012, 26, 125-125.

Center for Disease Control, Antibiotic Resistance Threats in the United States, 2013. *Medical Benefits.* 2014, 31, 12-12.

Johnston, B. L.; Bryce, E. Hospital infection control strategies for vancomycin-resistant *Enterococcus*, methicillin-resistant *Staphylococcus aureus* and *Clostridium difficile*. Can. Med. Assoc. J. 2009, 180, 627-631.

Goldmann, D. A.; Weinstein, R. A.; Wenzel, R. P.; Tablan, O. C.; Duma, R. J.; Gaynes, R. P.; Schlosser, J.; Martone, W. J. Strategies to prevent and control the emergence and spread of antimicrobial-resistant microorganisms in hospitals: A challenge to hospital leadership. J. Am. Med. Assoc. 1996, 275, 234-240.

Kumar Gautam, C.; Kumar Srivastav, A.; Bind, S.; Madhav, M.; Shanthi, V. An insight into biofilm ecology and its applied aspects. International Journal of Pharmacy and Pharmaceutical Sciences. 2013, 5, 69-73.

Larson, E. L.; Early, E.; Cloonan, P.; Sugrue, S.; Parides, M. An organizational climate intervention associated with increased handwashing and decreased nosocomial infections. Behavioral Medicine. 2000, 26, 14-22.

MacDonald, A.; Dinah, F.; MacKenzie, D.; Wilson, A. Performance feedback of hand hygiene, using alcohol gel as the skin decontaminant, reduces the number of inpatients newly affected by MRSA and antibiotic costs. J. Hosp. Infect. 2004, 56, 56-63.

Gerhard Domagk A new class of disinfectants. Dtsch med Wochenschr. 1935, 61, 829-832.

Ladow, J. E.; Warnock, D. C.; Hamill, K. M.; Simmons, K. L.; Davis, R. W.; Schwantes, C. R.; Flaherty, D. C.; Willcox, J. A. L.; Wilson-Henjum, K.; Caran, K. L.; Minbiole, K. P. C.; Seifert, K. Bicephalic amphiphile architecture affects antibacterial activity. Eur. J. Med. Chem. 2011, 46, 4219-4226.

Grenier, M. C.; Davis, R. W.; Wilson-Henjum, K. L.; LaDow, J. E.; Black, J. W.; Caran, K. L.; Seifert, K.; Minbiole, K. P. C. The antibacterial activity of 4,4'-bipyridinium amphiphiles with conventional, bicephalic and gemini architectures. Bioorg. Med. Chem. Lett. 2012, 22, 4055-4058.

Maisuria, B. B.; Actis, M. L.; Hardrict, S. N.; Falkinham III, J. O.; Cole, M. F.; Cihlar, R. L.; Peters, S. M.; Macri, R. V.; Sugandhi, E. W.; Williams, A. A.; Poppe, M. A.; Esker, A. R.; Gandour, R. D. Comparing micellar, hemolytic, and antibacterial properties of di- and tricarboxyl dendritic amphiphiles. Bioorg. Med. Chem. 2011, 19, 2918-2926.

Macri, R. V.; Karlovská, J.; Doncel, G. F.; Du, X.; Maisuria, B. B.; Williams, A. A.; Sugandhi, E. W.; Falkinham III, J. O.; Esker, A. R.; Gandour, R. D. Comparing anti-HIV, antibacterial, antifungal, micellar, and cytotoxic properties of tricarboxylato dendritic amphiphiles. Bioorg. Med. Chem. 2009, 17, 3162-3168.

Sugandhi, E. W.; Falkinham III, J. O.; Gandour, R. D. Synthesis and antimicrobial activity of symmetrical two-tailed dendritic tricarboxylato amphiphiles. Bioorg. Med. Chem. 2007, 15, 3842-3853.

Sugandhi, E. W.; Macri, R. V.; Williams, A. A.; Kite, B. L.; Slebodnick, C.; Falkinham, J. O.; Esker, A. R.; Gandour, R. D. Synthesis, Critical Micelle Concentrations, and Antimycobacterial Properties of Homologous, Dendritic Amphiphiles. Probing Intrinsic Activity and the "Cutoff" Effect. J. Med. Chem. 2007, 50, 1645-1650.

Williams, A. A.; Sugandhi, E. W.; Macri, R. V.; Falkinham, J. O.; Gandour, R. D. Antimicrobial activity of long-chain, water-soluble, dendritic tricarboxylato amphiphiles. Journal of Antimicrobial Chemotherapy. 2007, 59, 451-458.

Falkinham III, J. O.; Macri, R. V.; Maisuria, B. B.; Actis, M. L.; Sugandhi, E. W.; Williams, A. A.; Snyder, A. V.; Jackson, F. R.; Poppe, M. A.; Chen, L.; Ganesh, K.; Gandour, R. D. Antibacterial activities of dendritic amphiphiles against nontuberculous mycobacteria. Tuberculosis. 2012, 92, 173-181.

Ator, L. E.; Jennings, M. C.; McGettigan, A. R.; Paul, J. J.; Wuest, W. M.; Minbiole, K. P. C. Beyond paraquats: dialkyl 3,3'- and 3,4'-bipyridinium amphiphiles as antibacterial agents. Bioorg. Med. Chem. Lett. 2014, 24, 3706-3709.

Black, J. W.; Jennings, M. C.; Azarewicz, J.; Paniak, T. J.; Grenier, M. C.; Wuest, W. M.; Minbiole, K. P. C. TMEDA-derived biscationic amphiphiles: An economical preparation of potent antibacterial agents. Bioorg. Med. Chem. Lett. 2014, 24, 99-102.

Scamehorn, J. F.; Sabatini, D. A.; Harwell, J. H. Surfactants, Part I: Fundamentals. In Encyclopedia of Supramolecular ChemistryMarcel Dekker: New York, 2004; pp 1458.

Pohorille, A.; Deamer, D. Self-assembly and function of primitive cell membranes. Res. Microbiol. 2009, 160, 449-456.

Soontravanich, S.; Munoz, J. A.; Scamehorn, J. F.; Harwell, J. H.; Sabatini, D. A. Interaction between an anionic and an amphoteric surfactant. Part I: Monomer-micelle equilibrium. Journal of Surfactants and Detergents. 2008, 11, 251-261.

Haldar, J.; Kondaiah, P.; Bhattacharya, S. Synthesis and antibacterial properties of novel hydrolyzable cationic amphiphiles. Incorporation of multiple head groups leads to impressive antibacterial activity. J. Med. Chem. 2005, 48, 3823-3831.

Geraldo, I. M.; Gilman, A.; Shintre, M. S.; Modak, S. M. Rapid antibacterial activity of 2 novel hand soaps: evaluation of the risk of development of bacterial resistance to the antibacterial agents. Infect. Control Hosp. Epidemiol. 2008, 29, 736-741.

Hiraki, Y.; Yoshida, M.; Masuda, Y.; Inoue, D.; Tsuji, Y.; Kamimura, H.; Karube, Y.; Takaki, K.; Kawano, F. Successful treatment of skin and soft tissue infection due to carbapenem-resistant *Acinetobacter baumannii* by ampicillin-sulbactam and meropenem combination therapy. International Journal of Infectious Diseases. 2013, 17, e1234-e1236.

Sick, A. C.; Tschudin-Sutter, S.; Turnbull, A. E.; Weissman, S. J.; Tamma, P. D. Empiric Combination Therapy for Gram-Negative Bacteremia. Pediatrics. 2014.

Daikos, G. L.; Petrikkos, P.; Psichogiou, M.; Kosmidis, C.; Vryonis, E.; Skoutelis, A.; Georgousi, K.; Tzouvelekis, L. S.; Tassios, P. T.; Bamia, C.; Petrikkos, G. Prospective observational study of the impact of VIM-1 metallo-beta-lactamase on the outcome of patients with *Klebsiella pneumoniae* bloodstream infections. Antimicrob. Agents Chemother. 2009, 53, 1868-1873.

Drew, K. R. P.; Sanders, L. K.; Culumber, Z. W.; Zribi, O.; Wong, G. C. L. Cationic Amphiphiles Increase Activity of Aminoglycoside Antibiotic Tobramycin in the Presence of Airway Polyelectrolytes. J. Am. Chem. Soc. 2009, 131, 486-493.

Sattar, S., A.; Springthorpe, V., S.; Karim, Y.; Loro, P. Chemical disinfection of non-porous inanimate surfaces experimentally contaminated with four human pathogenic viruses. Epidemiol. Infect. 1989, 102, 493-505.

Harrison, J. J.; Turner, R. J.; Joo, D. A.; Stan, M. A.; Chan, C. S.; Allan, N. D.; Vrionis, H. A.; Olson, M. E.; Ceri, H. Copper and quaternary ammonium cations exert synergistic bactericidal and antibiofilm activity against *Pseudomonas aeruginosa*. Antimicrob. Agents Chemother. 2008, 52, 2870-2881.

Shintre, M. S.; Gaonkar, T. A.; Modak, S. M. Efficacy of an alcohol-based healthcare hand rub containing synergistic combination of farnesol and benzethonium chloride. Int. J. Hyg. Environ. Health. 2006, 209, 477-487.

Dymond, M. K.; Attard, G. S. Cationic type i amphiphiles as modulators of membrane curvature elastic stress in vivo. Langmuir. 2008, 24, 11743-11751.

Wiseman, T.; Williston, S.; Brandts, J. F.; Lin, L.-. Rapid measurement of binding constants and heats of binding using a new titration calorimeter. Anal. Biochem. 1989, 179, 131-137.

Kresheck, G. C.; Hargraves, W. A. Thermometric titration studies of the effect of head group, chain length, solvent, and temperature on the thermodynamics of Micelle formation. J. Colloid Interface Sci. 1974, 48, 481-493.

Paula, S.; Süs, W.; Tuchtenhagen, J.; Blume, A. Thermodynamics of micelle formation as a function of temperature: A high sensitivity titration calorimetry study. J. Phys. Chem. 1995, 99, 11742-11751.

Heerklotz, H.; Seelig, J. Titration calorimetry of surfactant-membrane partitioning and membrane solubilization. Biochimica et Biophysica Acta-Biomembranes. 2000, 1508, 69-85.

Meyer, R. D.; Young, L. S.; Armstrong, D. Tobramycin (nebramycin factor 6): in vitro activity against *Pseudomonas aeruginosa*. Appl. Microbiol. 1971, 22, 1147-1151.

Bodey, G. P.; Ho, D. H.; LeBlanc, B. In vitro studies of BMY-28142, a new broad-spectrum cephalosporin. Antimicrob. Agents Chemother. 1985, 27, 265-269.

Gellatly, S. L.; Hancock, R. E. W. *Pseudomonas aeruginosa*: new insights into pathogenesis and host defenses. Pathog Dis. 2013, 67, 159-173.

Motyl, M.; Dorso, K.; Barrett, J.; Giacobbe, R. Basic microbiological techniques used in antibacterial drug discovery. Curr Protoc Pharmacol. 2006, Chapter 13, Unit13A.3.

Giacometti, A.; Cirioni, O.; Del Prete, M. S.; Paggi, A. M.; D'Errico, M. M.; Scalise, G. Combination studies between polycationic peptides and clinically used antibiotics against Gram-positive and Gram-negative bacteria. Peptides. 2000, 21, 1155-1160.

Lister, P. D.; Wolter, D. J. Levofloxacin-Imipenem Combination Prevents the Emergence of Resistance among Clinical Isolates of *Pseudomonas aeruginosa*. Clinical Infectious Diseases. 2005, 40, S105-S114.

Hiraki, Y.; Yoshida, M.; Masuda, Y.; Inoue, D.; Tsuji, Y.; Kamimura, H.; Karube, Y.; Takaki, K.; Kawano, F. Successful treatment of skin and soft tissue infection due to carbapenem-resistant *Acinetobacter baumannii* by ampicillin-sulbactam and meropenem combination therapy. International Journal of Infectious Diseases. 2013, 17, e1234-e1236.

Gribble, M. J.; Chow, A. W.; Naiman, S. C.; Smith, J. A.; Bowie, W. R.; Sacks, S. L.; Grossman, L.; Buskard, N.;

Growe, G. H.; Plenderleith, L. H. Prospective randomized trial of piperacillin monotherapy versus carboxypenicillin-aminoglycoside combination regimens in the empirical treatment of serious bacterial infections. Antimicrob. Agents Chemother. 1983, 24, 388-393.

Best, M.; Kennedy, M. E.; Coates, F. Efficacy of a variety of disinfectants against *Listeria* spp. Appl. Environ. Microbiol. 1990, 56, 377-380.

Tebbs, S. E.; Elliott, T. S. A novel antimicrobial central venous catheter impregnated with benzalkonium chloride. J. Antimicrob. Chemother. 1993, 31, 261-271.

Price, P. B. Benzalkonium Chloride (Zephiran Chloride®) as a Skin Disinfectant. Archives of Surgery. 1950, 61, 23.

Seifert, K. N.; McArthur, W. P.; Bleiweis, A. S.; Brady, L. J. Characterization of group B streptococcal glyceraldehyde-3-phosphate dehydrogenase: surface localization, enzymatic activity, and protein-protein interactions. Can. J. Microbiol. 2003, 49, 350-356.

P. A. Wayne Methods for dilution antimicrobial tests for bacteria that grow aerobically. In, 8th ed.; 2009.

The inventive subject matter being thus described, it will be obvious that the same may be modified or varied in many ways. For example, antimicrobial compositions or therapeutic compositions comprising two or more compounds selected from any of the four general classes of compounds disclosed herein, in any combination, are expected to have beneficial antimicrobial or therapeutic properties and uses, including unexpected and synergistic properties as described in the Examples herein. Such modifications and variations are not to be regarded as a departure from the spirit and scope of the inventive subject matter and all such modifications and variations are intended to be included within the scope of the following claims.

We claim:
1. A compound of formula II

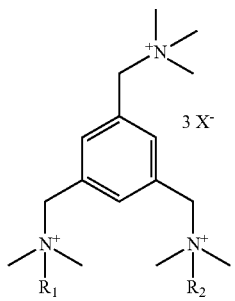

II

3 X⁻ or a biologically acceptable salt, ester, or solvate thereof, wherein:
$R_1$ is independently selected from the group consisting of straight or branched chain $C_n$ alkyl, alkenyl, or alkynyl;
$R_2$ is independently selected from the group consisting of straight or branched chain $C_m$ alkyl, alkenyl, or alkynyl;
X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;
m is a range of 2 to about 18; and
n is a range of 2 to about 18.

2. The compound of claim 1, wherein:
$R_1$ is independently selected from the group consisting of straight or branched chain $C_n$ alkyl; and
$R_2$ is independently selected from the group consisting of straight or branched chain $C_m$ alkyl.

3. The compound of claim 2, wherein:
$R_1$ is independently selected from the group consisting of straight chain $C_{2-18}$ alkyl; and
$R_2$ is independently selected from the group consisting of straight chain $C_{2-18}$ alkyl.

4. The compound of claim 3, wherein:
$R_1$ is independently selected from the group consisting of straight chain $C_{8-16}$ alkyl; and
$R_2$ is independently selected from the group consisting of straight chain $C_{8-16}$ alkyl.

5. The compound of claim 4, wherein:
$R_1$ is independently selected from the group consisting of straight chain $C_{10-14}$ alkyl; and
$R_2$ is independently selected from the group consisting of straight chain $C_{10-14}$ alkyl.

6. The compound of claim 5, wherein:
$R_1$ is $C_{12}$ alkyl; and
$R_2$ is $C_{12}$ alkyl.

7. The compound of claim 1, wherein X is $F^{(-)}$, $Cl^{(-)}$, $Br^{(-)}$, or $I^{(-)}$.

8. The compound of claim 7, wherein X is bromine.

9. A method for inhibiting bacterial growth, comprising contacting a bacteria with a composition comprising:
(a) a compound of Formula II

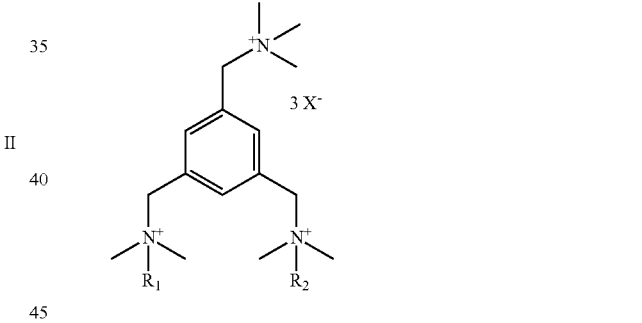

II

3 X⁻ or a biologically acceptable salt, ester, or solvate thereof, wherein:
$R_1$ is independently selected from the group consisting of straight or branched chain $C_n$ alkyl, alkenyl, or alkynyl;
$R_2$ is independently selected from the group consisting of straight or branched chain $C_m$ alkyl, alkenyl, or alkynyl;
X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_2CH_2CH_2CH_2CO_2^{(-)}$, other alkyl carboxylates, polyanions, and combinations thereof;
m is a range of 2 to about 18; and
n is a range of 2 to about 18, or
(b) a combination of two or more compounds, comprising:
i) a compound of formula II, and
ii) one or more additional compounds, each independently selected from the group consisting of a compound of Formula I

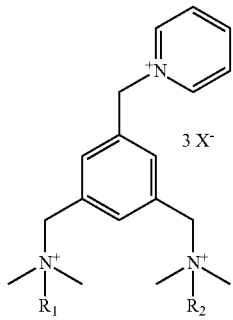

or a biologically acceptable salt, ester, or solvate thereof, wherein:

$R_1$ is independently selected from the group consisting of straight or branched chain $C_n$ alkyl, alkenyl, or alkynyl;

$R_2$ is independently selected from the group consisting of straight or branched chain $C_m$ alkyl, alkenyl, or alkynyl;

X is a counterion selected from the group consisting of $CO_3^{(2-)}$, $SO_4^{(2-)}$, $S_2O_3^{(2-)}$, $H_2PO_4^{(-)}$, $NO_3^{(-)}$, $F^{(-)}$, $Cl^{(-)}$, $Br^{(-)}$, $I^{(-)}$, $SCN^{(-)}$, $CH_3CO_2^{(-)}$, $CH_3CH_3CH_2CH_2CH_2CH_2CO_2^{(-)}$, other alkyl carboxylates, polyanions, and combinations thereof;

m is a range of 1 to about 22; and n is a range of 1 to about 22, and a compound of Formula II.

10. The method of claim 9, wherein said composition is in a solution in a suitable concentration for use as an environmental disinfectant.

11. The method of claim 9, wherein said composition is formulated for use as a topical personal care composition.

12. The method of claim 9, wherein said composition is formulated for use as a material coating.

* * * * *